United States Patent
Kim et al.

(10) Patent No.: US 9,903,867 B2
(45) Date of Patent: Feb. 27, 2018

(54) METHODS FOR PREDICTING AND IMPROVING THE SURVIVAL OF COLORECTAL CANCER PATIENTS

(71) Applicant: NESTEC S.A., Vevey (CH)

(72) Inventors: Phillip Kim, Irvine, CA (US); Anjali Jain, San Diego, CA (US); Sharat Singh, Rancho Santa Fe, CA (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/985,190

(22) Filed: Dec. 30, 2015

(65) Prior Publication Data

US 2016/0169898 A1 Jun. 16, 2016

Related U.S. Application Data

(63) Continuation of application No. PCT/IB2014/061606, filed on May 21, 2014.

(60) Provisional application No. 61/825,998, filed on May 21, 2013.

(51) Int. Cl.
*G01N 33/574* (2006.01)
*A61K 39/00* (2006.01)

(52) U.S. Cl.
CPC . *G01N 33/57419* (2013.01); *G01N 33/57492* (2013.01); *A61K 39/00* (2013.01); *A61K 2039/505* (2013.01); *G01N 2333/70596* (2013.01); *G01N 2333/912* (2013.01); *G01N 2333/91205* (2013.01); *G01N 2333/91215* (2013.01); *G01N 2440/14* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| 2004/0229294 | A1* | 11/2004 | Chan-Hui | G01N 33/542 435/7.2 |
| 2009/0258364 | A1* | 10/2009 | Goel | C12Q 1/6886 435/6.12 |
| 2012/0231965 | A1 | 9/2012 | Kim et al. | |

FOREIGN PATENT DOCUMENTS

WO 2012/119113 A2 9/2012

OTHER PUBLICATIONS

Salvatore et al., J Clin Oncol., 2010, 28(15), suppl. Abstract e14065.*
Custodio, A. et al., "Prognostic and predictive biomarkers for epidermal growth factor receptor-targeted therapy in colorectal cancer: Beyond KRAS mutations," Critical Reviews in Oncology/Hematology, http://dx.doi.org/10.1016/j.critrevonc.2012.05.001, 2012.
Lee, J. et al., "A novel proteomics-based clinical diagnostics technology identifies heterogeneity in activated signaling pathways in gastric cancers," PLOS One, 8(1):e54644, 2013.
Tsigris, C. et al., "Clinical significance of serum and urinary c-erbB-2 levels in colorectal cancer," Cancer Letters, 184(2):215-222, 2002.
Maksymowych, W. et al., "Etanercept exerts beneficial effects on articular cartilage biomarkers of degradation and turnover in patients with ankylosing spondylitis," Journal of Rheumatology, 32(10):1911-1917, 2005.

* cited by examiner

*Primary Examiner* — Hong Sang
(74) *Attorney, Agent, or Firm* — Kilpatrick Townsend & Stockton LLP

(57) ABSTRACT

The present invention provides assays and methods for predicting the survival of a subject having colorectal cancer (CRC), thereby determining whether the subject will have a good prognosis or poor prognosis. The present invention also provides assays and methods for predicting therapeutic efficacy and/or response to anti-cancer therapeutics in a subject having CRC, thereby selecting a therapeutic regimen to which the subject is likely to be responsive.

7 Claims, 19 Drawing Sheets

| Characteristics | (Total N=120)(%) |
|---|---|
| Age | |
|   Median age(range) | 61(31-85) |
|   ≤65 | 68(56.7) |
|   >65 | 52(43.3) |
| Sex | |
|   Male | 73(60.8) |
|   Female | 47(39.2) |
| Stage | |
|   I | 11(9.2) |
|   II | 38(31.7) |
|   III | 38(31.7) |
|   IV | 33(27.4) |
| Histology | |
|   WD | 8(6.7) |
|   MD | 99(82.5) |
|   PD | 5(4.1) |
|   Adenocarcinoma, not specified | 8(6.7) |
| Primary tumor | |
|   Colon | 73(60.8) |
|   Rectum | 47(39.2) |
| Curative resection | |
|   Yes | 108(90.0) |
|   No | 12(10.0) |
| Adjuvant chemotherapy(Colon) | |
|   5-FU based chemotherapy | 20(27.4) |
|   Capecitabine | 18(24.7) |
|   XELOX or XELIRI | 13(17.8) |
|   No adjuvant chemotherapy | 22(30.1) |
| Adjuvant chemotherapy(Rectum) | |
|   5-FU+RT | 28(59.6) |
|   XELOX+RT | 1(2.1) |
|   5-FU based chemotherapy | 2(4.3) |
|   XELODA | 1(2.1) |
|   No adjuvant chemotherapy | 15(31.9) |
| Tissue specimens (from 120 patients) | |
|   Primary(colon or rectum) | 116 |
|   Liver metastasis | 14(10 paired with primary) |
|   Peritoneal seeding | 1 (paired with primary) |
| KRAS mutational status | |
|   At least one mutation | 49 (42%) |
|   KRAS G12S | 3 |
|   KRAS G12D | 19 |
|   KRAS G12A | 1 |
|   KRAS G12V | 6 |
|   KRAS G12C | 7 |
|   KRAS G13D | 17 |

WD: Well differentiated; MD: Moderately differentiated; PD: Poorly differentiated.

*FIG. 2*

- KRAS WT (31/48): 65%
- KRAS G13Dmut (8/48): 17%
- KRAS G12mut (9/48): 19%

- Stage IV: 23%, Stage III: 27%, Stage II: 35%, Stage I: 10%
- 77% of the patients received chemotherapy.

[(pPI3K/pHER3)] ratio < 2/10 (n=48)
42% of total Sample cohort
Better Survival

- KRAS WT (39/67): 58%
- KRAS G13Dmut (9/67): 13%
- KRAS G12mut (19/67): 28%
- Majority of the KRAS G12mut tumors (68%), that have the worst prognosis in CRC, lie in this category.
- Stage IV: 22%, Stage III: 37%, Stage II: 31%, Stage I: 9%
- 69% of the patients received chemotherapy.

[(pPI3K/pHER3)] ratio > 2/10 (n=67)
58% of total Sample cohort
Worse Survival

FIG. 7 pPI3K/pHER1, pPI3K/pHER2, pPI3K/pHER3

All correlate negatively and significantly with relapse in CRC (Higher the marker, quicker is the relapse)

|  | pPI3K | pPI3K/pHER1 | pPI3K/pHER2 | pPI3K/pHER3 |
|---|---|---|---|---|
| Number of XY Pairs | 113 | 113 | 113 | 113 |
| Pearson r | -0.24 | -0.23 | -0.25 | -0.29 |
| 95% confidence interval | -0.41 to -0.06 | -0.40 to -0.05 | -0.42 to -0.07 | -0.45 to -0.12 |
| P value (one-tailed) | 0.0054 | 0.0069 | 0.00 | 0.00 |
| P value summary | ** | ** | ** | *** |
| R square | 0.06 | 0.05 | 0.06 | 0.09 | pPI3K/pHER1, pPI3K/pHER2, pPI3K/pHER3

All correlate negatively and significantly with disease free survival (DFS) in CRC

| Parameter | pPI3K/p-HER3 | pPI3K/pHER1 | pPI3K/pHER2 |
|---|---|---|---|
| Number of XY Pairs | 113 | 113 | 113 |
| Pearson r | -0.17 | -0.19 | -0.17 |
| 95% confidence interval | -0.3464 to 0.01253 | -0.3654 to -0.00928 | -0.3415 to 0.01800 |
| P value (one-tailed) | 0.034 | 0.0199 | 0.0382 |
| P value summary | * | * | * |
| Is the correlation significant? (alpha=0.05) | Yes | Yes | Yes |
| R square | 0.030 | 0.038 | 0.028 |

FIG. 18

METHODS FOR PREDICTING AND IMPROVING THE SURVIVAL OF COLORECTAL CANCER PATIENTS

CROSS-REFERENCE TO RELATED APPLICATION

This application is a continuation of PCT/IB2014/061606 filed May 21, 2014, which application claims priority to U.S. Provisional Application No. 61/825,998, filed May 21, 2013, the disclosures of which are hereby incorporated by reference in their entirety for all purposes.

BACKGROUND OF THE INVENTION

The process of signal transduction in cells is responsible for a variety of biological functions including, but not limited to, cell division and death, metabolism, immune cell activation, neurotransmission, and sensory perception to name but a few. Accordingly, derangements in normal signal transduction in cells can lead to a number of disease states such as diabetes, heart disease, autoimmunity, and cancer.

One well characterized signal transduction pathway is the MAP kinase pathway, which is responsible for transducing the signal from epidermal growth factor (EGF) to the promotion of cell proliferation in cells. EGF binds to a transmembrane receptor-linked tyrosine kinase, the epidermal growth factor receptor (EGFR), which is activated by the binding of EGF. The binding of EGF to EGFR activates the tyrosine kinase activity of the cytoplasmic domain of the receptor. One consequence of this kinase activation is the autophosphorylation of EGFR on tyrosine residues. The phosphorylated tyrosine residues on the activated EGFR provide a docking site for the binding of SH2 domain containing adaptor proteins such as GRB2. In its function as an adaptor, GRB2 further binds to a guanine nucleotide exchange factor, SOS, by way of an SH3 domain on GRB2. The formation of the complex of EGFR-GRB2-SOS leads to SOS activation to a guanine nucleotide exchange factor that promotes the removal of GDP from Ras. Upon removal of GDP, Ras binds GTP and becomes activated.

Following activation, Ras binds to and activates the protein kinase activity of RAF kinase, a serine/threonine-specific protein kinase. What follows is the activation of a protein kinase cascade that leads to cell proliferation. In outline, RAF kinase then phosphorylates and activates MEK, another serine/threonine kinase. Activated MEK phosphorylates and activates mitogen-activated protein kinase (MAPK). Among the targets for further phosphorylation by MAPK are 40S ribosomal protein S6 kinase (RSK). The phosphorylation of RSK by MAPK results in activation of RSK, which in turn phosphorylates ribosomal protein S6. Another known target of MAPK is the proto-oncogene, c-Myc, a gene important for cell proliferation, which is mutated in a variety of cancers. MAPK also phosphorylates and activates another protein kinase, MNK, which in turn phosphorylates the transcription factor, CREB. Indirectly, MAPK also regulates the transcription of the Fos gene, which encodes yet another transcription factor involved in cell proliferation. By altering the levels and activities of such transcription factors, MAPK transduces the original extracellular signal from EGF into altered transcription of genes that are important for cell cycle progression.

Given the central role that signal transduction pathways play in cell growth, it is not surprising that many cancers arise as a result of mutations and other alterations in signal transduction components that result in aberrant activation of cell proliferation pathways. For example, overexpression or hyperactivity of EGFR has been associated with a number of cancers, including glioblastoma multiforme, colon cancer, and lung cancer. This has prompted the development of anticancer therapeutics directed against EGFR, including gefitinib and erlotinib for lung cancer, and cetuximab for colon cancer.

Cetuximab is an example of a monoclonal antibody inhibitor, which binds to the extracellular ligand binding domain of EGFR, thus preventing the binding of ligands which activate the EGFR tyrosine kinase. In contrast, gefitinib and erlotinib are small molecules which inhibit the intracellularly-located EGFR tyrosine kinase. In the absence of kinase activity, EGFR is unable to undergo autophosphorylation at tyrosine residues, which is a prerequisite for binding of downstream adaptor proteins, such as GRB2. By halting the signaling cascade in cells that rely on this pathway for growth, tumor proliferation and migration is diminished.

Additionally, other studies have shown that about 70% of human melanomas and a smaller fraction of other tumors have a point mutation (V599E) in the Raf gene which leads to persistent activation of the MAPK pathway (see, e.g., Davies et al., *Nature*, 417:949-954 (2002)). Such results suggest that mutations in particular signal transduction pathways may be characteristic of particular types of tumors and that such specific, altered signal transduction pathways may be a promising target for chemotherapeutic intervention.

Given that different cancer treatments, particularly cancer chemotherapy, may function either directly or indirectly by means of either blocking or activating cellular signal transduction pathways involved in cell proliferation or death, respectively, the expression and/or activation of a given signal transduction pathway in a particular form of cancer such as, for example, colorectal cancer may serve as a good indicator of the efficacy of various cancer treatments. Accordingly, in addition to fulfilling other needs, the present invention provides a method for evaluating the effectiveness of potential anticancer therapies for an individual patient with colorectal cancer. As such, the present invention provides methods for assisting a physician in selecting a suitable cancer therapy for the treatment of colorectal cancer at the right dose and at the right time for every patient.

SUMMARY OF THE INVENTION

The present invention provides assays and methods for predicting the survival of a subject having colorectal cancer (CRC), thereby determining whether the subject will have a good prognosis (e.g., disease-free survival) or poor prognosis (e.g., disease recurrence), e.g., after tumor surgery. The present invention also provides assays and methods for predicting therapeutic efficacy and/or response to anti-cancer therapeutics such as anti-HER therapies, anti-PI3K therapies, anti-cMET therapies, or combinations thereof in a subject having CRC, thereby selecting a therapeutic regimen to which the subject is likely to be responsive. The present invention further provides methods for treating a subject with CRC by administering a specific therapeutic regimen tailored to the signal transduction biomarkers that are activated in the CRC tumor. In particular embodiments, the methods of the present invention rely on the detection of the activation state or level of a specific combination of signal transduction analytes in a cancer cell obtained from a subject having CRC. Thus, the methods described herein are particularly useful for predicting the survival or prognosis of a subject with CRC and for guiding treatment decisions both pre-tumor and post-tumor surgery by identifying a subject who would benefit from therapy that is specifically tailored to the signal transduction biomarkers that are activated in the CRC tumor.

In some aspects, the present invention provides a method for predicting the survival of a subject having colorectal cancer (CRC), e.g., after tumor surgery, comprising:

(a) determining a PI3K/HER index based upon the activation (e.g., phosphorylation) levels of PI3K and a HER receptor (e.g., a pPI3K/pHER3 index) in a cellular extract produced from an isolated cancer cell; and (b) predicting the survival of the subject based upon the PI3K/HER index relative to a (first) reference index cut-off (e.g., a PI3K/HER reference cut-off ratio).

In some embodiments, the HER receptor is selected from the group consisting of HER1, HER2, HER3, and combinations thereof. In particular embodiments, the method comprises determining a PI3K/HER1 index, a PI3K/HER2 index, a PI3K/HER3 index, or combinations thereof. In some instances, the method comprises determining a PI3K/HER3 index alone or in combination with a PI3K/HER1 index and/or a PI3K/HER2 index.

In certain embodiments, the subject is predicted to have a good prognosis with a longer period or length of time of survival without disease recurrence (e.g., higher disease-free survival or DFS) when the determined PI3K/HER index is less than the reference index cut-off. In some instances, the subject has a wild-type KRAS genotype or a G13D mutation in the KRAS oncogene. In particular instances, the reference index cut-off comprises a value of about 0.2 (e.g., about 20% or 2/10). In other instances, the reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10).

In certain embodiments, the subject is predicted to have a poor prognosis with a shorter period or length of time of survival without disease recurrence (e.g., lower disease-free survival or DFS) when the determined PI3K/HER index is less than the reference index cut-off. In some instances, the subject has a G12 mutation in the KRAS oncogene. Non-limiting examples of G12 mutations in the KRAS oncogene include a G12S, G12D, G12A, G12V, G12R, and G12C mutation. In particular instances, the reference index cut-off comprises a value of about 0.2 (e.g., about 20% or 2/10). In other instances, the reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10).

In certain embodiments, the subject is predicted to have a poor prognosis with a shorter period or length of time of survival without disease recurrence (e.g., lower disease-free survival or DFS) when the determined PI3K/HER index is greater than the reference index cut-off. In some instances, the subject has a wild-type KRAS genotype or a G13D or G12 mutation in the KRAS oncogene. Non-limiting examples of G12 mutations in the KRAS oncogene include a G12S, G12D, G12A, G12V, G12R, and G12C mutation. In particular instances, the reference index cut-off comprises a value of about 0.2 (e.g., about 20% or 2/10). In other instances, the reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10).

In other embodiments, the method further comprises predicting that the subject has a good prognosis with a longer period or length of time of survival without disease recurrence (e.g., higher disease-free survival or DFS) when the activation (e.g., phosphorylation) level of PI3K is low relative to the activation (e.g., phosphorylation) level of the HER receptor (e.g., pPI3K level is about 15% to about 30% of pHER3 expression).

In certain embodiments, the method further comprises determining a HER1/cMET index based upon the levels of HER1 and cMET (e.g., expression or activation (e.g., phosphorylation) levels of HER1 and cMET) in a cellular extract produced from the isolated cancer cell and further predicting the survival of the subject based upon the HER1/cMET index relative to a second reference index cut-off (e.g., a HER1/cMET reference cut-off ratio). In such embodiments, the subject is predicted to have a good prognosis with a longer period or length of time of survival without disease recurrence (e.g., higher disease-free survival or DFS) when the determined PI3K/HER index is less than the first reference index cut-off (e.g., less than the PI3K/HER reference index cut-off) and the determined HER1/cMET index is greater than the second reference index cut-off (e.g., the HER1/cMET reference cut-off ratio). In other embodiments, the subject is predicted to have a poor prognosis with a shorter period or length of time of survival without disease recurrence (e.g., lower disease-free survival or DFS) when the determined PI3K/HER index is less than the first reference index cut-off (e.g., less than the PI3K/HER reference index cut-off) and the determined HER1/cMET index is less than the second reference index cut-off (e.g., the HER1/cMET reference cut-off ratio). In further embodiments, the subject is predicted to have a poor prognosis with a shorter period or length of time of survival without disease recurrence (e.g., lower disease-free survival or DFS) when the determined PI3K/HER index is greater than the first reference index cut-off (e.g., greater than the PI3K/HER reference index cut-off) and the determined HER1/cMET index is less than the second reference index cut-off (e.g., the HER1/cMET reference cut-off ratio). In particular instances, the (first) PI3K/HER reference index cut-off comprises a value of about 0.2 (e.g., about 20% or 2/10). In other instances, the (first) PI3K/HER reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10). In other particular instances, the (second) HER1/cMET reference index cut-off comprises a value of about 2. In yet other instances, the (second) HER1/cMET reference index cut-off comprises a value of about 3, 4, 5, 6, 7, 8, 9, 10, or more.

In other aspects, the present invention provides a method for selecting a therapy for the treatment of colorectal cancer (CRC) in a subject, e.g., after tumor surgery, comprising:

(a) determining a PI3K/HER index based upon the activation (e.g., phosphorylation) levels of PI3K and a HER receptor (e.g., a pPI3K/pHER3 index) in a cellular extract produced from an isolated cancer cell; and (b) selecting a suitable therapy (e.g., an anti-EGFR therapy, anti-PI3K therapy, an anti-HER2 therapy, an anti-HER3 therapy, an anti-cMET therapy, and/or therapy with a targeting agent that inhibits a molecule that drives PI3K activation) for the treatment of the CRC in the subject based upon the PI3K/HER index relative to a (first) reference index cut-off (e.g., a PI3K/HER reference cut-off ratio).

In some embodiments, the HER receptor is selected from the group consisting of HER1, HER2, HER3, and combinations thereof. In particular embodiments, the method comprises determining a PI3K/HER1 index, a PI3K/HER2 index, a PI3K/HER3 index, or combinations thereof. In some instances, the method comprises determining a PI3K/

HER3 index alone or in combination with a PI3K/HER1 index and/or a PI3K/HER2 index.

In certain embodiments, the subject is predicted to be responsive to an anti-EGFR therapy when the determined PI3K/HER index is less than the reference index cut-off. In some instances, the subject has a wild-type KRAS genotype or a G13D mutation in the KRAS oncogene. In particular instances, the reference index cut-off comprises a value of about 0.2 (e.g., about 20% or 2/10). In other instances, the reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10).

In certain embodiments, the subject is predicted to be non-responsive to an anti-EGFR therapy when the determined PI3K/HER index is less than the reference index cut-off. In some instances, the subject has a G12 mutation in the KRAS oncogene. Non-limiting examples of G12 mutations in the KRAS oncogene include a G12S, G12D, G12A, G12V, G12R, and G12C mutation. In particular instances, the reference index cut-off comprises a value of about 0.2 (e.g., about 20% or 2/10). In other instances, the reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10).

In certain embodiments, the subject is predicted to be non-responsive to an anti-EGFR therapy when the determined PI3K/HER index is greater than the reference index cut-off. In some instances, the subject has a wild-type KRAS genotype or a G13D or G12 mutation in the KRAS oncogene. Non-limiting examples of G12 mutations in the KRAS oncogene include a G12S, G12D, G12A, G12V, G12R, and G12C mutation. In particular instances, the reference index cut-off value comprises a value of about 0.2 (e.g., about 20% or 2/10). In other instances, the reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10).

In other embodiments, the method further comprises predicting that the subject will likely be responsive to an anti-EGFR therapy when the activation (e.g., phosphorylation) level of PI3K is low relative to the activation (e.g., phosphorylation) level of the HER receptor (e.g., pPI3K level is about 15% to about 30% of pHER3 expression).

In certain embodiments, the method further comprises determining a HER1/cMET index based upon the levels of HER1 and cMET (e.g., expression or activation (e.g., phosphorylation) levels of HER1 and cMET) in a cellular extract produced from the isolated cancer cell and further selecting a therapy for the treatment of the CRC based upon the HER1/cMET index relative to a second reference index cut-off (e.g., a HER1/cMET reference cut-off ratio). In such embodiments, the subject is predicted to be responsive to an anti-EGFR therapy when the determined PI3K/HER index is less than the first reference index cut-off (e.g., less than the PI3K/HER reference index cut-off) and the determined HER1/cMET index is greater than the second reference index cut-off (e.g., the HER1/cMET reference cut-off ratio). In other embodiments, the subject is predicted to be non-responsive to an anti-EGFR therapy when the determined PI3K/HER index is less than the first reference index cut-off (e.g., less than the PI3K/HER reference index cut-off) and the determined HER1/cMET index is less than the second reference index cut-off (e.g., the HER1/cMET reference cut-off ratio). In further embodiments, the subject is predicted to be non-responsive to an anti-EGFR therapy when the determined PI3K/HER index is greater than the first reference index cut-off (e.g., greater than the PI3K/HER reference index cut-off) and the determined HER1/cMET index is less than the second reference index cut-off (e.g., the HER1/cMET reference cut-off ratio). In particular instances, the (first) PI3K/HER reference index cut-off comprises a value of about 0.2 (e.g., about 20% or 2/10). In other instances, the (first) PI3K/HER reference index cut-off comprises a value of about 0.1 (e.g., about 10% or 1/10), about 0.3 (e.g., about 30% or 3/10), about 0.4 (e.g., about 40% or 4/10), or about 0.5 (e.g., about 50% or 5/10). In other particular instances, the (second) HER1/cMET reference index cut-off comprises a value of about 2. In yet other instances, the (second) HER1/cMET reference index cut-off comprises a value of about 3, 4, 5, 6, 7, 8, 9, 10, or more.

In particular embodiments, the best candidates for anti-EGFR therapy are subjects having CRC with a low pPI3K/pHER index (e.g., less than the PI3K/HER reference index cut-off), but a high HER1/cMET index (e.g., greater than the HER1/cMET reference index cut-off).

In further embodiments, an anti-pPI3K therapy in addition to or instead of an anti-EGFR therapy is more suitable for aggressive CRC tumors that have pPI3K signaling greater than about 15 to about 30% of pHER (e.g., pHER3). Such tumors include, but are not limited to, KRAS-WT tumors with high pPI3K signaling, the majority of KRAS-G12mut tumors, CRC tumors that have metastasized regardless of their KRAS mutational status, etc. In other embodiments, an anti-cMET therapy in addition to or instead of an anti-EGFR therapy, with or without anti-PI3K therapy, is more suitable for the treatment of aggressive CRC tumors that have pPI3K greater than about 15 to about 30% of pHER (e.g., pHER3). Such tumors include, but are not limited to, KRAS-WT tumors with high pPI3K signaling, the majority of KRAS-G12mut tumors, CRC tumors that have metastasized regardless of their KRAS mutational status, etc.

In some instances, the anti-EGFR therapy includes monoclonal antibodies such as cetuximab, panitumumab, matuzumab, and nimotuzumab; tyrosine kinase inhibitors such as erlotinib (Tarceva®), lapatinib (GW-572016; Tykerb®), gefitinib (Iressa®), canertinib (CI 1033), and BIBW-2992; and combinations thereof.

In other instances, the anti-PI3K therapy includes PX-866, wortmannin, LY 294002, quercetin, tetrodotoxin citrate, thioperamide maleate, GDC-0941 (957054-30-7), IC87114, PI-103, PIK93, BEZ235 (NVP-BEZ235), TGX-115, ZSTK474, (−)-deguelin, NU 7026, myricetin, tandutinib, GDC-0941 bismesylate, GSK690693, KU-55933, MK-2206, OSU-03012, perifosine, triciribine, XL-147, PIK75, TGX-221, NU 7441, PI 828, XL-765, and WHI-P 154, as well as combinations thereof.

In other instances, the anti-HER2 therapy includes monoclonal antibodies such as trastuzumab (Herceptin®) and pertuzumab (2C4); small molecule tyrosine kinase inhibitors such as gefitinib (Iressa®), erlotinib (Tarceva®), pelitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof.

In other instances, the anti-HER3 therapy includes monoclonal antibodies such as MM-121, U3-1287 (AMG 888), MEHD7945A, and pertuzumab (2C4); bispecific antibodies such as MM-111; small molecule inhibitors such as MP-470 (amuvatinib), AZD8931, and canertinib (CI 1033); and combinations thereof.

In other instances, the anti-cMET therapy includes neutralizing antibodies, such as MAG102 (Amgen) and Met- Mab (Roche), as well as tyrosine kinase inhibitors (TKIs), such as ARQ197, XL184, PF-02341066, GSK1363089/XL880, MP470, MGCD265, SGX523, PF04217903 JNJ38877605, INCB28060, AMG-458, E7050, MK-2461, and BMS-777607, and combinations thereof.

Non-limiting examples of molecules that activate PI3K and their targeting agents include the following signal transduction molecules and inhibitors thereof:

| Molecule | Inhibitor | Target |
|---|---|---|
| FGFR family of receptors (FGFR1,2,3,4) | AZD4547 | targets FGFR1-3, Bcr-Abl |
| | Ponatinib | targets FGFR1-4, RET, PDGFR, Flt3, KIT, VEGFR2 |
| | Dovitinib | targets FGFR1-3, PDGFR, VEGFR, Flt3, KIT |
| | BGJ398 | targets FGFR1-3, |
| | E-3810 | targets FGFR1-2, VEGFR |
| | JNJ-42756493 | |
| | A RQ087 | |
| HGF | A MG102 (rilotumumab) | |
| | SCH900105 | |
| | TAK-701 | |
| | L2G7 | |
| Ron Kinase | MGCD2S5 | targets cMET/RON/VEGFR/Tie2 |
| | PHA 665752 | targets cMET/RON |
| | Compound 1 (Amgen) | targets cMET/RON |
| | GSK1363089 (foretinib) | targets cMET/KDR/RON |
| VEGFR | MGCD2S5 | targets cMET/RON/VEGFR/Tie2 |
| | Dovitinib | targets FGFR1-3, PDGFR, VEGFR, Flt3, KIT |
| | Ponatinib | targets FGFR1-4, RET, PDGFR, Flt3, KIT, VEGFR2 |
| | E-3810 | targets FGFR1-2, VEGFR |
| Tie2 | MGCD2S5 | targets cMET/RON/VEGFR/Tie2 |
| KDR | GSK1363089 (foretinib) | targets cMET/KDR/RON |
| RET | Ponatinib | targets FGFR1-4, RET, PDGFR, Flt3, KIT, VEGFR2 |
| Flt3 | Ponatinib | targets FGFR1-4, RET, PDGFR, Flt3, KIT, VEGFR2 |
| | Dovitinib | targets FGFR1-3, PDGFR, VEGFR, Flt3, KIT |
| Kit | Ponatinib | targets FGFR1-4, RET, PDGFR, Flt3, KIT, VEGFR2 |
| | Dovitinib | targets FGFR1-3, PDGFR, VEGFR, Flt3, KIT |
| PDGFR | Ponatinib | targets FGFR1-4, RET, PDGFR, Flt3, KIT, VEGFR2 |
| | Dovitinib | targets FGFR1-3, PDGFR, VEGFR, Flt3, KIT |
| IGF1R | Figitumumab (CP-751, 871) | |
| | R1507 | |
| | Cixutumumab (IMC-A 12) | |
| | Dalotuzumab (MK-0646) | |
| | OSI-906 | |
| | Gamitumab | |

In certain instances, the molecule that drives PI3K activation includes K-Ras, H-Ras, other Ras family small GTPases, Rho family small GTPases (e.g., Rac, Cdc42, RhoG), and combinations thereof. In other instances, the targeting agent that inhibits the molecule that drives PI3K activation includes ML141 (Cdc42/Rac1 inhibitor), AZA1 (Cdc42/Rac1 inhibitor), ZCL278 (Cdc42 inhibitor), NSC23766 (Rac inhibitor), EHop-016/CAS 1380432-32-5 (Rac inhibitor), CAS 1090893-12-1 (Rac inhibitor), CAS 1177865-17-6 (Rac inhibitor), EHT 1864 (Rac inhibitor), W56 (Rac1 inhibitor), salirasib (Ras inhibitor), and combinations thereof.

In certain embodiments, the methods of the invention further comprise determining the (total) expression and/or activation (e.g., phosphorylation) levels and/or status of one or more additional analytes such as one or more of the signal transduction molecules described herein.

Total expression and activation (e.g., phosphorylation) levels and/or status of signal transduction molecules can be determined using any of a variety of techniques. In certain embodiments, the expression and/or activation (e.g., phosphorylation) level and/or status of signal transduction molecules in samples such as cellular extracts of cancer cells is detected with an immunoassay such as a single detection assay or a proximity dual detection assay (e.g., a Collaborative Enzyme Enhanced Reactive Immunoassay (CEER™)) as described herein.

The CEER™ technology is described herein and in the following patent documents, which are each herein incorporated by reference in their entirety for all purposes: PCT Patent Publication Nos. WO 2008/036802, WO 2009/012140, WO 2009/108637, WO 2010/132723, WO 2011/008990, and WO 2011/050069; and PCT Application No. PCT/US2011/066624.

Other objects, features, and advantages of the present invention will be apparent to one of skill in the art from the following detailed description and figures.

BRIEF DESCRIPTION OF THE DRAWINGS

FIG. 2 shows the characteristics of the CRC patients enrolled in the study.

FIG. 7 shows the composition of CRC tumors segregated by the pPI3K/pHER3 index.

FIG. 18 shows that pPI3K/pHER1, pPI3K/pHER2, and pPI3K/pHER3 ratios all correlate negatively and significantly with relapse (e.g., the higher the marker, the quicker the relapse) and disease free survival (DFS) in CRC.

DETAILED DESCRIPTION OF THE INVENTION

I. Introduction

Figure 1:
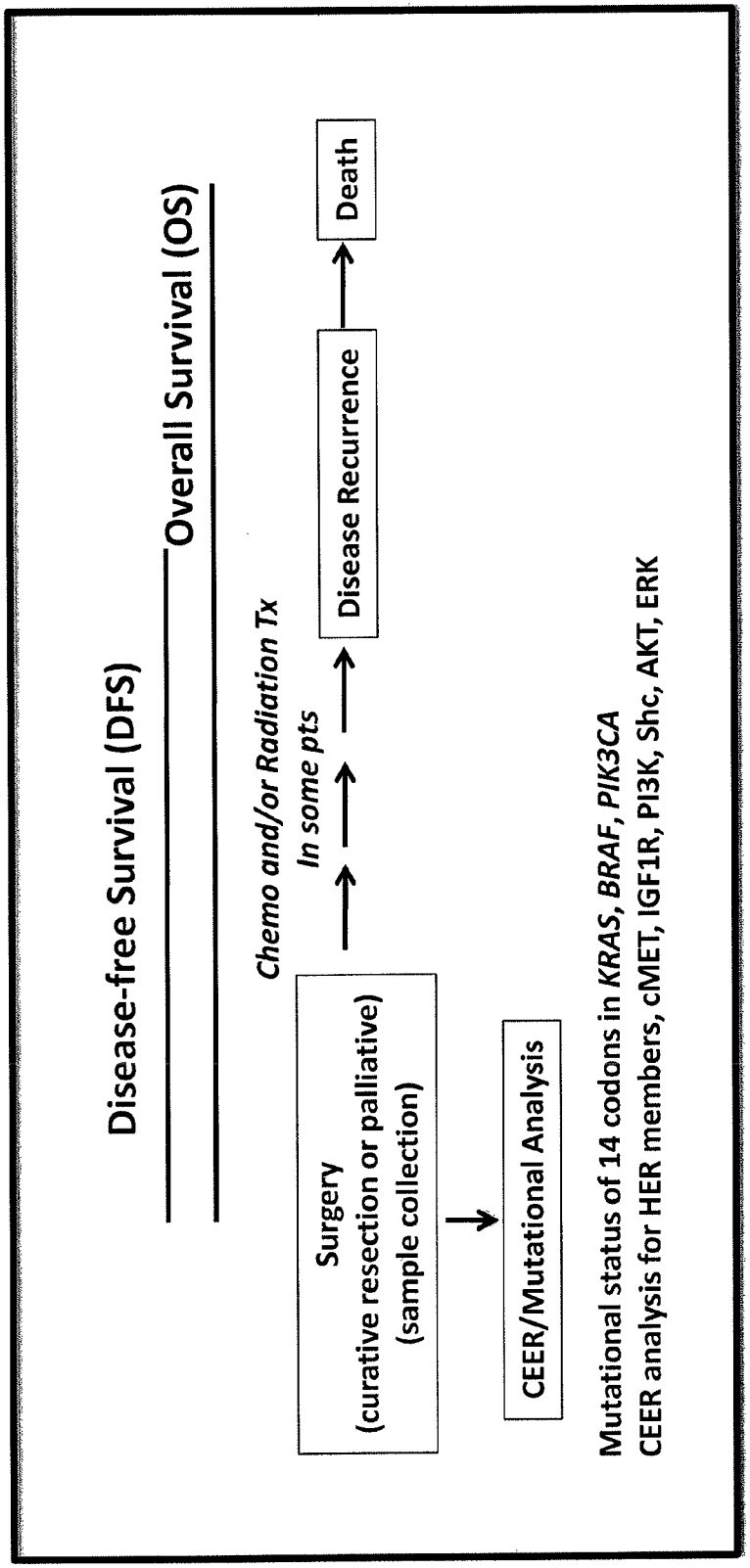
FIG. 1 shows the CRC cohort study schema for the study described in Example 1.

The present invention provides assays and methods for predicting the survival of a subject having colorectal cancer (CRC), thereby determining whether the subject will have a good prognosis (e.g., disease-free survival) or poor prognosis (e.g., disease recurrence), e.g., after tumor surgery. The present invention also provides assays and methods for predicting therapeutic efficacy and/or response to anti-cancer therapeutics such as anti-HER therapies, anti-PI3K therapies, anti-cMET therapies, or combinations thereof in a subject having CRC, thereby selecting a therapeutic regimen to which the subject is likely to be responsive. The present invention further provides methods for treating a subject with CRC by administering a specific therapeutic regimen tailored to the signal transduction biomarkers that are activated in the CRC tumor. In particular embodiments, the methods of the present invention rely on the detection of the activation state or level of a specific combination of signal transduction analytes in a cancer cell obtained from a subject having CRC. Thus, the methods described herein are particularly useful for predicting the survival or prognosis of a subject with CRC and for guiding treatment decisions both pre-tumor and post-tumor surgery by identifying a subject who would benefit from therapy that is specifically tailored to the signal transduction biomarkers that are activated in the CRC tumor.

Example 1 demonstrates that the ratio of phospho-PI3K (pPI3K) to phospho-HER3 (pHER3) in colorectal cancer (CRC) tumors, regardless of their KRAS status, predicts tumor prognosis and anti-EGFR therapy outcome. As described herein, the best candidates for anti-EGFR therapies may be CRCs with a low pPI3K/pHER3 ratio but a high HER1/cMET ratio.

As described in Example 1, when the pPI3K/pHER3 index is above the cut-off ratio (e.g., pPI3K/pHER3>20%), pPI3K signaling is greater than HER signaling and the CRC is classified as PI3K-driven. In terms of prognosis, patients with a pPI3K/pHER3 index above the cut-off ratio are predicted to have a low DFS regardless of KRAS mutational status. In terms of CRC therapy selection, patients with a pPI3K/pHER3 index above the cut-off ratio are likely to be non-responsive to anti-EGFR therapies and have a higher likelihood of being responsive to anti-PI3K therapies. When the pPI3K/pHER3 index is below the cut-off ratio (e.g., pPI3K/pHER3<20%), HER signaling is higher and the CRC is classified as HER-driven. In terms of prognosis, patients with a pPI3K/pHER3 index below the cut-off ratio are predicted to have higher DFS when the KRAS status is WT or G13D, but a lower DFS when the KRAS status is KRAS G12mut. In terms of CRC therapy selection, some of the patients with a pPI3K/pHER3 index below the cut-off ratio are likely to be responsive to anti-EGFR therapies.

As further described in Example 1, in HER-driven CRC tumors with higher HER signaling than cMET signaling (e.g., HER1>cMET; high HER1/cMET index or low cMET signaling), CRC patients with a wild-type or G13D KRAS status have a good prognosis (e.g., higher DFS) and are more likely to respond to anti-EGFR therapies. However, in HER-driven CRC tumors with lower HER1 signaling (e.g., HER1<cMET; low HER1/cMET index or high cMET signaling), CRC patients with a G12 KRAS mutation have a poor prognosis (e.g., lower DFS).

Thus, Example 1 shows that CEER-based signaling pathway profiles revealed novel molecular subsets of CRCs beyond the KRAS mutation-based segregations. Such molecular segregations can guide novel therapeutic selection strategies for CRCs. In particular, it was discovered that the ratio of pPI3K to pHER3 expression (a pPI3K/pHER3 index) in CRC tumors predicts tumor prognosis and anti-EGFR therapy outcome, regardless of their KRAS status. The best candidates for anti-EGFR therapies were identified as CRCs with a low pPI3K/pHER3 ratio but a high HER1/cMET ratio. A secondary selection of CRC tumors that have low pPI3K signaling (e.g., about 15-30% of pHER3 expression) can further predict CRC tumors with the best prognosis possibly anti-EGFR therapy outcome regardless of their KRAS status. Anti-pPI3K therapies in addition to or instead of anti-EGFR therapies are more suitable for aggressive CRC tumors that have pPI3K signaling greater than about 15-30% of pHER3. Such tumors include, but are not limited to, KRAS-WT tumors with high pPI3K signaling, the majority of KRAS-G12mut tumors, CRC tumors that have metastasized regardless of their KRAS mutational status, etc. This study also found that increased pPI3K signaling may be due to increased cMET signaling in some CRCs. Anti-cMET therapies in addition to or instead of anti-EGFR therapies, with or without anti-PI3K therapies, may be useful for the treatment of aggressive CRC tumors that have pPI3K greater than about 15-30% of pHER3. Such tumors include, but are not limited to, KRAS-WT tumors with high pPI3K signaling, majority of KRAS-G12mut tumors, CRC tumors that have metastasized regardless of their KRAS mutational status, etc.

Moreover, Example 1 demonstrates that pPI3K/pHER1 and pPI3K/pHER2 ratios also correlate negatively and significantly with relapse (e.g., the higher the marker, the quicker the relapse) and disease free survival (DFS) in CRC. Notably, Example 1 further demonstrates that pPI3K/pHER1 and pPI3K/pHER2 ratios are higher in CRC samples that have higher pPI3K/pHER3 ratios (e.g., above the reference pPI3K/pHER3 index cut-off).

Accordingly, the present invention also provides methods for selecting appropriate therapies to downregulate one or more deregulated signal transduction pathways involved in colorectal cancer. Therefore, the present invention may be used to facilitate the design of personalized therapies based on the particular molecular signature provided by the collection of total and/or activated signal transduction proteins, alone or in combination with somatic mutation analysis, in a given patient's colorectal tumor.

II. Definitions

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, digestive and gastrointestinal cancers such as colorectal cancer, gastric cancer (e.g., stomach cancer), gastrointestinal stromal tumors (GIST), gastrointestinal carcinoid tumors, colon cancer, rectal cancer, anal cancer, bile duct cancer, small intestine cancer, and esophageal cancer; breast cancer; lung cancer (e.g., non-small cell lung cancer (NSCLC)); gallbladder cancer; liver cancer; pancreatic cancer; appendix cancer; prostate cancer, ovarian cancer; renal cancer (e.g., renal cell carcinoma); cancer of the central nervous system; skin cancer; lymphomas; gliomas; choriocarcinomas; head and neck cancers; osteogenic sarcomas; and blood cancers. As used herein, a "tumor" comprises one or more cancerous cells.

The term "analyte" includes any molecule of interest, typically a macromolecule such as a polypeptide, whose presence, amount (expression level), activation state, and/or identity is determined.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR1/FLT1, VEGFR2/FLK1/KDR, VEGFR3/FLT4, FLT3/FLK2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, c-MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, and RTK 106; truncated forms of receptor tyrosine kinases such as truncated HER2 receptors with missing amino-terminal extracellular domains (e.g., p95ErbB2 (p95m), p110, p95c, p95n, etc.), truncated cMET receptors with missing amino-terminal extracellular domains, and truncated HER3 receptors with missing amino-terminal extracellular domains; receptor tyrosine kinase dimers (e.g., p95HER2/HER3; p95HER2/HER2; truncated HER3 receptor with HER1, HER2, HER3, or HER4; HER2/HER2; HER3/HER3; HER2/HER3; HER1/HER2; HER1/HER3; HER2/HER4; HER3/HER4; etc.); non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, phosphatase and tensin homolog (PTEN), SGK3, 4E-BP1, P70S6K (e.g., p70 S6 kinase splice variant alpha I), protein tyrosine phosphatases (e.g., PTP1B, PTPN13, BDP1, etc.), RAF, PLA2, MEKK, JNKK, JNK, p38, Shc (p66), Ras (e.g., K-Ras, N-Ras, H-Ras), Rho, Rac1, Cdc42, PLC, PKC, p53, cyclin D1, STAT1, STAT3, phosphatidylinositol 4,5-bisphosphate (PIP2), phosphatidylinositol 3,4,5-trisphosphate (PIP3), mTOR, BAD, p21, p27, ROCK, IP3, TSP-1, NOS, GSK-3β, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

The term "activation state" refers to whether a particular signal transduction molecule is activated. Similarly, the term "activation level" refers to what extent a particular signal transduction molecule is activated. The activation state typically corresponds to the phosphorylation, ubiquitination, and/or complexation status of one or more signal transduction molecules. Non-limiting examples of activation states (listed in parentheses) include: HER1/EGFR (EGFRvIII, phosphorylated (p-) EGFR, EGFR:Shc, ubiquitinated (u-) EGFR, p-EGFRvIII); ErbB2 (p-ErbB2, p95HER2 (truncated ErbB2), p-p95HER2, ErbB2:Shc, ErbB2:PI3K, ErbB2:EGFR, ErbB2:ErbB3, ErbB2:ErbB4); ErbB3 (p-ErbB3, truncated ErbB3, ErbB3:PI3K, p-ErbB3:PI3K, ErbB3:Shc); ErbB4 (p-ErbB4, ErbB4:Shc); c-MET (p-c-MET, truncated c-MET, c-Met:HGF complex); AKT1 (p-AKT1); AKT2 (p-AKT2); AKT3 (p-AKT3); PTEN (p-PTEN); P70S6K (p-P70S6K); MEK (p-MEK); ERK1 (p-ERK1); ERK2 (p-ERK2); PDK1 (p-PDK1); PDK2 (p-PDK2); SGK3 (p-SGK3); 4E-BP1 (p-4E-BP1); PIK3R1 (p-PIK3R1); c-KIT (p-c-KIT); ER (p-ER); IGF-1R (p-IGF-1R, IGF-1R:IRS, IRS:PI3K, p-IRS, IGF-1R:PI3K); INSR (p-INSR); FLT3 (p-FLT3); HGFR1 (p-HGFR1); HGFR2 (p-HGFR2); RET (p-RET); PDGFRA (p-PDGFRA); PDGFRB (p-PDGFRB); VEGFR1 (p-VEGFR1, VEGFR1:PLCγ, VEGFR1:Src); VEGFR2 (p-VEGFR2, VEGFR2:PLCγ, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); TIE1 (p-TIE1); TIE2 (p-TIE2); EPHA (p-EPHA); EPHB (p-EPHB); GSK-3β (p-GSK-3β); NFKB (p-NFKB), IKB (p-IKB, p-P65:IKB); BAD (p-BAD, BAD:14-3-3); mTOR (p-mTOR); Rsk-1 (p-Rsk-1); Jnk (p-Jnk); P38 (p-P38); STAT1 (p-STAT1); STAT3 (p-STAT3); FAK (p-FAK); RB (p-RB); Ki67; p53 (p-p53); CREB (p-CREB); c-Jun (p-c-Jun); c-Src (p-c-Src); paxillin (p-paxillin); GRB2 (p-GRB2), Shc (p-Shc), Ras (p-Ras), GAB1 (p-GAB1), SHP2 (p-SHP2), GRB2 (p-GRB2), CRKL (p-CRKL), PLCγ (p-PLCγ), PKC (e.g., p-PKCα, p-PKCβ, p-PKCδ), adducin (p-adducin), RB1 (p-RB1), and PYK2 (p-PYK2).

The term "oncogene" includes a gene that has the potential to cause cancer. Non-limiting examples of oncogenes include growth factors or mitogens such as c-Sis; receptor tyrosine kinases such as EGFR, HER2, PDGFR, and VEGFR; cytoplasmic tyrosine kinases such as Abl and kinases in the Src-family, Syk-ZAP-70 family, and BTK family of tyrosine kinases; cytoplasmic serine/threonine kinases and their regulatory subunits such as PIK3CA, PIK3R1, and RAF (e.g., RAF-1, A-RAF, B-RAF); regulatory GTPases such as RAS (e.g., KRAS); transcription factors such as MYC; and combinations thereof.

The term "KRAS mutation" includes any one or more mutations in the KRAS (which can also be referred to as KRAS2 or RASK2) gene. Examples of KRAS mutations include, but are not limited to, G12S, G12D, G12A, G12V, G12R, G12C, G13D, and combinations thereof.

The term "BRAF mutation" includes any one or more mutations in the BRAF (which can also be referred to as serine/threonine-protein kinase B-Raf or B-Raf) gene. Examples of BRAF mutations include, but are not limited to, V600E, R461I, I462S, G463E, G463V, G465A, G465E, G465V, G468A, G468E, N580S, E585K, D593V, F594L, G595R, L596V, T598I, V599D, V599E, V599K, V599R, K600E, A727V, and combinations thereof.

The term "PIK3CA mutation" includes any one or more mutations in the PIK3CA (which can also be referred to as PI3K or p110-alpha) gene. Examples of PIK3CA mutations include, but are not limited to, E545A, E545G, E545K, Q546E, Q546K, H1047R, H1047L, 3204insA, and combinations thereof.

The term "EGFR mutation" includes any one or more mutations in the EGFR (which can also be referred to as HER1 or ErbB1) gene. Examples of EGFR mutations include, but are not limited to, deletions in exon 19 such as L858R, G719S, G719S, G719C, L861Q and S768I, as well as insertions in exon 20 such as T790M, and combinations thereof.

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein refers to the ability of an assay to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, ascites, pleural efflux, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), a tissue sample (e.g., tumor tissue) such as a surgical resection of a tumor, and cellular extracts thereof. In some embodiments, the sample is whole blood or a fractional component thereof such as plasma, serum, or a cell pellet. In other embodiments, the sample is obtained by isolating circulating cells of a solid tumor from whole blood or a cellular fraction thereof using any technique known in the art. In yet other embodiments, the sample is a formalin fixed paraffin embedded (FFPE) tumor tissue sample, e.g., from a solid tumor such as colorectal cancer. In particular embodiments, the sample is a tumor lysate or extract prepared from frozen tissue obtained from a subject having colorectal cancer.

The term "subject" or "patient" or "individual" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays described herein typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract. In particular embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, AKT, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. In particular embodiments, activation state-dependent antibodies are useful for detecting one or more sites of phosphorylation in one or more of the following signal transduction molecules (phosphorylation sites correspond to the position of the amino acid in the human protein sequence): EGFR/HER1/ErbB1 (e.g., tyrosine (Y) 1068); ErbB2/HER2 (e.g., Y1248); ErbB3/HER3 (e.g., Y1289); ErbB4/HER4 (e.g., Y1284); c-Met (e.g., Y1003, Y1230, Y1234, Y1235, and/or Y1349); SGK3 (e.g., threonine (T) 256 and/or serine (S) 422); 4E-BP1 (e.g., T70); ERK1 (e.g., T185, Y187, T202, and/or Y204); ERK2 (e.g., T185, Y187, T202, and/or Y204); MEK (e.g., S217 and/or S221); PIK3R1 (e.g., Y688); PDK1 (e.g., S241); P70S6K (e.g., T229, T389, and/or S421); PTEN (e.g., S380); AKT1 (e.g., S473 and/or T308); AKT2 (e.g., S474 and/or T309); AKT3 (e.g., S472 and/or T305); GSK-3β (e.g., S9); NFKB (e.g., S536); IKB (e.g., S32); BAD (e.g., S112 and/or S136); mTOR (e.g., S2448); Rsk-1 (e.g., T357 and/or S363); Jnk (e.g., T183 and/or Y185); P38 (e.g., T180 and/or Y182); STAT3 (e.g., Y705 and/or S727); FAK (e.g., Y397, Y576, 5722, Y861, and/or S910); RB (e.g., S249, T252, 5612, and/or S780); RB1 (e.g., S780); adducin (e.g., S662 and/or S724); PYK2 (e.g., Y402 and/or Y881); PKCα (e.g., S657); PKCα/β (e.g., T368 and/or T641); PKCδ (e.g., T505); p53 (e.g., S392 and/or S20); CREB (e.g., S133); c-Jun (e.g., S63); c-Src (e.g., Y416); and paxillin (e.g., Y31 and/or Y118).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

The term "incubating" is used synonymously with "contacting" and "exposing" and does not imply any specific time or temperature requirements unless otherwise indicated.

"Receptor tyrosine kinases" or "RTKs" include a family of fifty-six (56) proteins characterized by a transmembrane domain and a tyrosine kinase motif. RTKs function in cell signaling and transmit signals regulating growth, differentiation, adhesion, migration, and apoptosis. The mutational activation and/or overexpression of receptor tyrosine kinases transforms cells and often plays a crucial role in the development of cancers. RTKs have become targets of various molecularly targeted agents such as trastuzumab, cetuximab, gefitinib, erlotinib, sunitinib, imatinib, nilotinib, and the like. One well-characterized signal transduction pathway is the MAP kinase pathway, which is responsible for transducing the signal from epidermal growth factor (EGF) to the promotion of cell proliferation in cells.

The term "gene" and variants thereof includes the segment of DNA involved in producing a polypeptide chain; it includes regions preceding and following the coding region, such as the promoter and 3'-untranslated region, respectively, as well as intervening sequences (introns) between individual coding segments (exons).

The term "genotype" and variants thereof refers to the genetic composition of an organism, including, for example, whether a diploid organism is heterozygous or homozygous for one or more variant alleles of interest.

The term "polymorphism" and variants thereof refers to the occurrence of two or more genetically determined alternative sequences or alleles in a population. A "polymorphic site" refers to the locus at which divergence occurs. Preferred polymorphic sites have at least two alleles, each occurring at a particular frequency in a population. A polymorphic locus may be as small as one base pair (e.g., single nucleotide polymorphism or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances." The allele occurring most frequently in a selected population can sometimes be referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest or in the alternative the variant allele may have no effect on the enzymatic activity of an encoded protein.

The term "single nucleotide polymorphism (SNP)" and variants thereof refers to a change of a single nucleotide within a polynucleotide, including within an allele. This can include the replacement of one nucleotide by another, as well as deletion or insertion of a single nucleotide. Most typically, SNPs are biallelic markers, although tri- and tetra-allelic markers can also exist. By way of non-limiting example, a nucleic acid molecule comprising SNP A\C may include a C or A at the polymorphic position. For combinations of SNPs, the term "haplotype" is used, e.g., the genotype of the SNPs in a single DNA strand that are linked to one another. In some embodiments, the term "haplotype" can be used to describe a combination of SNP alleles, e.g., the alleles of the SNPs found together on a single DNA molecule. In further embodiments, the SNPs in a haplotype can be in linkage disequilibrium with one another.

The terms "disease-free survival" and "DFS" as used herein include the length of time after treatment for a specific disease (e.g., cancer) during which a patient survives with no sign of the disease (e.g., without known recurrence). In certain embodiments, disease-free survival is a clinical parameter used to evaluate the efficacy of a particular therapy, which is usually measured in units of 1 or 5 years.

The term "progression-free survival" includes the length of time during and after treatment for a specific disease (e.g., cancer) in which a patient is living with the disease without additional symptoms of the disease.

The term "overall survival" includes the clinical endpoint describing patients who are alive for a defined period of time after being diagnosed with or treated for a disease, such as cancer.

III. Description of the Embodiments

The present invention provides compositions and methods for detecting the status (e.g., expression and/or activation levels) of components of signal transduction pathways in tumor cells from a colorectal cancer. In certain embodiments, the present invention further comprises detecting (e.g., genotyping for) the presence (or absence) of one or more somatic mutations (e.g., single nucleotide polymorphisms (SNPs)) in tumor cells from a colorectal cancer. In certain aspects, the present invention also provides compositions and methods for selecting appropriate therapies to downregulate or shut down one or more deregulated signal transduction pathways. Thus, certain embodiments of the invention may be used to facilitate the design of personalized therapies based on the particular molecular signature provided by the collection of total and activated signal transduction proteins and/or somatic mutations in a given patient's tumor (e.g., colorectal cancer).

In particular aspects, the present invention provides molecular markers (biomarkers) that enable the determination or prediction of whether a colorectal cancer can respond or is likely to respond favorably to an anticancer drug. In specific embodiments, measuring the level of expression and/or activation of at least one or more of HER1, HER2, HER3, cMET, cKIT, IGF-1R, PI3K, AKT, ERK, and/or SHC is particularly useful for selecting a suitable anticancer drug and/or identifying or predicting a response thereto in cells such as colorectal cancer cells (e.g., isolated cancer cells from a colorectal tumor). In other embodiments, the methods of the invention further comprise genotyping for the presence or absence of one or more variant alleles (e.g., somatic mutations) in genes such as KRAS, BRAF, and/or PIK3CA (e.g., at one, two, three, four, five, or more polymorphic sites such as a SNP in one or more of these genes). In particular embodiments, the determination of the presence or absence of the variant allele in conjunction with the determination of the expression level and/or activation level of one or more analytes further aids or improves the selection of a suitable anticancer drug and/or the identification or prediction of a response thereto in cells such as colorectal cancer cells (e.g., isolated cancer cells from a colorectal tumor).

In some aspects, the present invention provides a method for predicting the survival of a subject having colorectal cancer (CRC), e.g., after tumor surgery, comprising:

(a) determining a PI3K/HER index based upon the activation (e.g., phosphorylation) levels of PI3K and a HER receptor (e.g., a pPI3K/pHER3 index) in a cellular extract produced from an isolated cancer cell; and (b) predicting the survival of the subject based upon the PI3K/HER index relative to a (first) reference index cut-off (e.g., a PI3K/HER reference cut-off ratio).

In other aspects, the present invention provides a method for selecting a therapy for the treatment of colorectal cancer (CRC) in a subject, e.g., after tumor surgery, comprising:

(a) determining a PI3K/HER index based upon the activation (e.g., phosphorylation) levels of PI3K and a HER receptor (e.g., a pPI3K/pHER3 index) in a cellular extract produced from an isolated cancer cell; and (b) selecting a suitable therapy (e.g., an anti-EGFR therapy, anti-PI3K therapy, an anti-HER2 therapy, an anti-HER3 therapy, an anti-cMET therapy, and/or therapy with a targeting agent that inhibits a molecule that drives PI3K activation) for the treatment of the CRC in the subject based upon the PI3K/HER index relative to a (first) reference index cut-off (e.g., a PI3K/HER reference cut-off ratio).

In certain embodiments, the methods of the invention further comprise determining the (total) expression and/or activation (e.g., phosphorylation) levels and/or status of one or more additional analytes such as one or more of the signal transduction molecules described herein.

To preserve the in situ activation states, signal transduction proteins are typically extracted shortly after the cells are isolated, preferably within 96, 72, 48, 24, 6, or 1 hr, more preferably within 30, 15, or 5 minutes. The isolated cells may also be incubated with growth factors usually at nanomolar to micromolar concentrations for about 1-30 minutes to resuscitate or stimulate signal transducer activation (see, e.g., Irish et al., Cell, 118:217-228 (2004)). Stimulatory growth factors include epidermal growth factor (EGF), heregulin (HRG), TGF-α, PIGF, angiopoietin (Ang), NRG1, PGF, TNF-α, VEGF, PDGF, IGF, FGF, HGF, cytokines, and the like. To evaluate potential anticancer therapies for an individual patient, the isolated cells can be incubated with one or more anticancer drugs of varying doses prior to, during, and/or after growth factor stimulation. Growth factor stimulation can be performed for a few minutes or hours (e.g., about 1-5 minutes to about 1-6 hours). After isolation, treatment with the anticancer drug, and/or growth factor stimulation, the cells are lysed to extract the signal transduction proteins using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the lysate can be stored at −80° C. until use.

In some embodiments, the anticancer drug comprises an agent that interferes with the function of one or more activated signal transduction pathway components in cancer cells. Non-limiting examples of such agents include those listed below in Table 1.

TABLE 1

| EGFR (ErbB1) (A) | HER-2 (ErbB2) (C) | HER-3 (ErbB3) (E) | HER-4 (ErbB4) target |
|---|---|---|---|
| Cetuximab<br>Panitumumab<br>Matuzumab<br>Nimotuzumab<br>ErbB1 vaccine | Trastuzumab<br>(Herceptin ®)<br>Pertuzumab (2C4)<br>BMS-599626*<br><br>*Heterodimerization HER-1/2;<br>Phase 1 | Antibody (U3) | |
| EGFR (ErbB1) (B) | HER-2 (ErbB2) (D) | ErbB1/2 (F) | ErbB1/2/4 (G) |
| Erlotinib<br>Gefitinib<br>EKB 569*<br>CL-387-785**<br>*(Wyeth, Irreversible, II CRC)<br>**(Wyeth, Irreversible, Preclinical) | CP-724714 (Pfizer) | Lapatinib (Tykerb ®)<br>HKI-272*<br>HKI-357 (Preclinical)<br>BIBW 2992**<br>*Wyeth, Irreversible, I/II NSCLC, Breast<br>**Boehringer Ingelheim, Irreversible, I/II Prostate, | Canertinib*<br>ARRY-334543<br>JNJ-26483327<br>JNJ-26483327<br>*Pfizer, Irreversible, II NSCLC, Breast |

TABLE 1-continued

|  |  | Ovarian, Breast |  |
| --- | --- | --- | --- |
| Raf (H) | SRC (H) | Mek: (I) | NFkB-IkB (I) |
| Sorafenib<br>PLX4032 (Plexxikon) | AZ | PD-325901 (II: NSCLC)<br>AZD6244 - Array/Az<br>XL518 Exelisis/DNA |  |
| mTor (J) | PI3K (J) | VEGFR2 and VEGFR1 (K) | VEGFR1/2/3: |
| Rad 001: Everolimus*<br>Temsirolimus<br>AP-23573*<br>*Everolimus (Novartis, combination with Gefetinib/Erlotinib; I/II: NSCLC, Glioblastoma)<br>Temsirolimus (Wyeth, combination with Gefetinib/Erlotinib; I/II: NSCLC, Glioblastoma)<br>*AP-23573 (Ariad, I/II: Endometrial) | PX-866*<br><br>*P110alpha specific inhibition; ProIX Pharma; Preclinical NSCLC | Avastin (DNA)<br>HuMV833*<br>VEGF-Trap**<br>*(PDL) anti-VEGFa<br>**Regeneron/Aventis (Receptor mimic) (Phase 2) | AZD 2171 (NSCLC, CRC)<br>AMG-706 (+ PDGFR) |
|  | VEGFR2 target (L) |  | EPH A-D |
| DC101*<br>IMC-IC11<br>IMC1121B Fully humanized<br>CDP-791*<br>Pazopanib****<br>*Imclone (Phase 2/3?)<br>Chimeric IgG1 against VEGFR2<br>*Celltech, pegalated di-Fab antibody against R2<br>****GSK, Multiple myeloma, ovarian, RCC Phase 3 enrollment completed, sarcoma II) | CDP-791 (UCB)<br>CP-547632*<br>AG13736<br>E-7080 (Eisai)<br>CHIR-258*<br>OSI-930 (+ cKit, PDGFR)<br>*OSI, PFIZER: (+ ErbB1 + PDGFR) (NSCLC, Ovarian Phase 2)<br>Pfizer: VEGFR1,2 and PDGFRbeta) (RCC II)<br>*(VEGFR1,2 FGFR3, PDGFR) | Bay-579352 (+ PDGFR)<br>ABT-869*<br>BMS-540215 (+FGFR1)<br>KRN-951<br>BBIW<br><br>*(+CSF1R, Erk, Flt-3, PDGFR) |  |
| VEGFR 2/ErbB1/2 (ErbB1)/cMet/FGFR (M) | VEGFR2/3/Raf/PDGFR/cKit/Flt-3 (N) | TIE 1/2 | VEGFR2/1/3, Flt-3, cFMS, PDGFR/cKit (O) |
| ZD6474*<br>XL647<br>AEE 788*<br><br><br><br><br><br><br><br><br>*(vandetanib) (Phase III: thyroid, NSCLC)<br>(Exelixis; Also EPHB2): (Patient resistant to Erlotinib; Asian patients) (Phase 2)<br>*(Novartis, Phase1/2) | Sorafenib*<br><br><br><br><br><br><br><br><br><br><br>*(RCC, HCC, NSCLC(III), Melanoma(III)) |  | PTK787 (Not cFMS, FLT-3)<br>Sunitinib<br>XL-999<br>SU-6668 (Pfizer)<br>GSK<br>AZ (AZD2171)<br>BMS<br>Novartis (AEE-788)<br>Amgen<br>Others |
| PDGFR target (P) | Abl target: (Q) | FTL 3 | RET |
| Tandutinib<br>Nilotinib | Imatinib<br>Dasatinib<br>Nilotinib<br>AT-9283<br>AZD-0530<br>Bosutinib |  |  |
| Kit target (R) | HGFR1/2 | FGFR1-4 | IGF-1R Target (S) |
| AMG-706<br>XL-880<br>XL-999 |  | Chiron | Merck<br>Pfizer<br>Novartis |

TABLE 1-continued

| HSP90 inhibitors: | Anti-Mitotic Drugs: | Other targets: |
|---|---|---|
| IPI-504* | Docetaxel* | HDAC inhibitors |
| 17-AAG** | Paclitaxel** | BCL2 |
| | Vinblastine, Vincristine, Vinorelbine*** | Chemotherapeutics (breakdown) |
| | | Proteosome inhibitors |
| *(Infinity Pharma, Mutant ErbB1, I/II multiple myeloma, GIST) | *(Microtubule stabilizer; Adjuvant and advanced Breast cancer; NSCLC, Androgen independent Prostate cancer) | |
| **(Kosan, I/II solid tumors) | **(Microtubule stabilizer; Adjuvant and advanced Breast cancer; NSCLC, Ovarian cancer, AIDS related Kaposi sarcoma) | |
| | ***(Microtubule De-stabilizers) | |

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the isolated cells are treated with one or more anti-signaling agents, anti-proliferative agents, and/or hormonal therapeutic agents in combination with at least one chemotherapeutic agent.

Examples of anti-signaling agents suitable for use in the present invention include, without limitation, monoclonal antibodies such as trastuzumab (Herceptin®), pertuzumab (2C4), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), imatinib mesylate (Gleevec®), leflunomide (SU101), vandetanib (ZACTIMA™; ZD6474), pelitinib, CP-654577, CP-724714, HKI-272, PKI-166, AEE788, BMS-599626, HKI-357, BIBW 2992, ARRY-334543, JNJ-26483327, and JNJ-26483327; and combinations thereof.

Exemplary anti-proliferative agents include mTOR inhibitors such as sirolimus (rapamycin), temsirolimus (CCI-779), everolimus (RAD001), BEZ235, and XL765; AKT inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)methyl)-4-piperidinyl)-2H-benzimidazol-2-one, 10-(4'-(N-diethylamino)butyl)-2-chlorophenoxazine, 3-formylchromone thiosemicarbazone (Cu(II)Cl$_2$ complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125: 1144-1145 (2003) and Kau et al., *Cancer Cell*, 4:463-476 (2003); PI3K inhibitors such as PX-866, wortmannin, LY 294002, quercetin, tetrodotoxin citrate, thioperamide maleate, GDC-0941 (957054-30-7), IC87114, P1-103, PIK93, BEZ235 (NVP-BEZ235), TGX-115, ZSTK474, (−)-deguelin, NU 7026, myricetin, tandutinib, GDC-0941 bismesylate, GSK690693, KU-55933, MK-2206, OSU-03012, perifosine, triciribine, XL-147, PIK75, TGX-221, NU 7441, PI 828, XL-765, and WHI-P 154; MEK inhibitors such as PD98059, ARRY-162, RDEA119, U0126, GDC-0973, PD184161, AZD6244, AZD8330, PD0325901, and ARRY-142886; and combinations thereof.

Non-limiting examples of pan-HER inhibitors include PF-00299804, neratinib (HKI-272), AC480 (BMS-599626), BMS-690154, PF-02341066, HM781-36B, CI-1033, BIBW-2992, and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines useful in the present invention include ANYARA from Active Biotech, DCVax-LB from Northwest Biotherapeutics, EP-2101 from IDM Pharma, GV1001 from Pharmexa, IO-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Non-limiting examples of HER2 inhibitors include monoclonal antibodies such as trastuzumab (Herceptin®) and pertuzumab (2C4); small molecule tyrosine kinase inhibitors such as gefitinib (Iressa®), erlotinib (Tarceva®), pelitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof.

Non-limiting examples of c-Met inhibitors include monoclonal antibodies such as AMG102 and MetMAb; small molecule inhibitors of c-Met such as ARQ197, JNJ-38877605, PF-04217903, SGX523, GSK 1363089/XL880, XL184, MGCD265, and MK-2461; and combinations thereof.

Non-limiting examples of signal transduction molecules and pathways that may be interrogated using the present invention include those shown in Table 2.

TABLE 2

| | | | | | | | |
|---|---|---|---|---|---|---|---|
| Pathway 1 | ErbB1 | ErbB1 Phospho | ErbB1 Shc | ErbB1 ubiquitin | ErbB1-PI3K | PTEN | |
| Pathway 2 | ErbB1 | ErbB1 VIII | ErbB1 VIII Phospho | ErbB1 VIII Shc | ErbB1 VIII ubiquitin | ErbB1 VIII PI3K | PTEN |
| Pathway 3 | ErbB2 | ErbB2 Phospho | HER-2 Shc | ErbB2: PI3K Complex | ErbB2 ubiquitin | PTEN | |
| Pathway 4 | ErbB2 | P95Truncated ErbB2 | ErbB2Phospho | P95Truncated ERBB2 Phospho | HER-2 Shc | ERBB2: PI3K Complex | ErbB2 ubiquitin | P95ErbB2: PI3K |
| Pathway 5 | ErbB3 | ErbB3 Phospho | ErbB3: PI3K Complex | ErbB3 PI3K Phospho | ErbB3: Shc | | |
| Pathway 6 | ErbB4 | ErbB4 Phospho | ErbB4: Shc | | | | |
| Pathway 7 | IGF-1R | IGF-1RPhospho | IGF-1R: IRS | IRS: PI3K | Phospho IRS | IGF-1R: PI3K | |
| Pathway 8 | INSR | INSRPhospho | | | | | |
| Pathway 9 | KIT | KIT Phospho | | | | | |
| Pathway 10 | FLT3 | FLT3Phospho | | | | | |
| Pathway 11 | HGFR 1 | HGFR 1 Phospho | | | | | |
| Pathway 12 | HGFR 2 | HGFR 2 Phospho | | | | | |
| Pathway 13 | RET | RET Phospho | | | | | |
| Pathway 14 | PDGFR alpha | PDGFR alpha Phospho | | | | | |
| Pathway 15 | PDGFR beta | PDGFR beta Phospho | | | | | |
| Pathway 16 | VEGFR 1 | VEGFR 1 Phospho | VEGFR 1: PLCγcomplex | VEGFR 1: Src | | | |
| Pathway 17 | VEGFR 2 | VEGFR 2 Phospho | VEGFR 2: PLCγ complex | VEGFR 2: Src | VEGFR-2/heparin sulphate complex | VEGFR-2, VE-cadherin complex | |
| Pathway 18 | VEGFR 3 | VEGFR 3 Phospho | | | | | |
| Pathway 19 | FGFR 1 | FGFR 1 Phospho | | | | | |
| Pathway 20 | FGFR 2 | FGFR 2 Phospho | | | | | |
| Pathway 21 | FGFR 3 | FGFR 3 Phospho | | | | | |
| Pathway 22 | FGFR 4 | FGFR 4 Phospho | | | | | |
| Pathway 23 | TIE 1 | TIE 1 Phospho | | | | | |
| Pathway 24 | TIE 2 | TIE 2 Phospho | | | | | |
| Pathway 25 | EPHA | EPHA Phospho | | | | | |
| Pathway 26 | EPHB | EPHB Phospho | | | | | |
| Pathway 27 | NFκB-IkB complex | phospho-IκB (S32) Total IkB | Total NFκB Phospho NFκB(S536) | Total P65 IkBa Phospho P65 IkBa | | | |
| Pathway 28 | ER | Phospho ER | ER-AIB1 | Other ER complexes | | | |
| Pathway 29 | PR | Phospho Pr | | PR complexes | | | |
| Pathway 30 | Hedgehog Pathway | | | | | | |
| Pathway 31 | Wnt pathway | | | | | | |
| Pathway 32 | Notch Pathway | | | | | | |

TABLE 2-continued

| Pathway 33 | Total Mek Phospho Mek (S217/S221) | Total Erk Phospho Erk (T202/Y204) | Total Rsk-1 Phospho Rsk-1 (T357/S363) | Total Stat3 Phospho Stat-3 (Y705) (S727) Total Stat 1 Phospho Stat1 (Y 701) | Phospho Bad (S112) Bad (total) | Total Fak Phospho Fak (Y576) | Total cSrc Phospho cSrc(Y416) | Total Ras Phospho Ras |
|---|---|---|---|---|---|---|---|---|
| Pathway 34 | Akt (Total) Phospho Akt (T473) | Phospho Akt (T308) | Phospho Bad (S112) Bad (total) | Phospho Bad (S136) | Bad: 14-3-3 complex | Total mTor Phospho mTor (S2448) | Total p70S6K Phospho p70S6K (T229) (T389) | GSK3beta Total (Phospho Ser 9) |
| Pathway 35 | Total Jnk Phospho Jnk (T183/Y185) | Total P38 Phospho P38 (T180/Y182) | Total Rb Phospho Rb (S249/T252) Phospho Rb (S780) | Total p53 Phospho p53 (S392) Phospho p53 (S20) | phospho-CREB(S133) Total CREB | Total c-Jun phospho-c-Jun; (S63) | Total Paxillin Phospho Paxillin (Y118) | |
| Pathway 36 | Ki67 | Cleaved Caspase 3, 8, 9 others | TOPO2 | | | | | |
| Pathway 37 | TGFbeta | | | | | | | |

Non-limiting examples of analytes such as signal transduction molecules that can be interrogated for expression (e.g., total amount) levels and/or activation (e.g., phosphorylation) levels in a cellular extract include receptor tyrosine kinases, non-receptor tyrosine kinases, tyrosine kinase signaling cascade components, nuclear hormone receptors, nuclear receptor coactivators, nuclear receptor repressors, and combinations thereof.

In one embodiment, the methods of the present invention comprise determining the expression level (e.g., total amount) and/or activation level (e.g., level of phosphorylation or complex formation) of at least one or more of the following analytes in a cellular extract: (1) HER1/EGFR/ErbB1; (2) HER2/ErbB2; (3) p95HER2 (truncated HER2); (4) HER3/ErbB3; (5) c-Met; (6) IGF1R; (7) cKit; (8) PI3K (e.g., PIK3CA and/or PIK3R1); (9) Shc; (10) Akt; (11) p70S6K; (12) VEGFR (e.g., VEGFR1, VEGFR2, and/or VEGFR3) and/or PDGFR (e.g., PDGFRA and/or PDGFRB); and (13) Erk (e.g., Erk1 (MAPK3) and/or Erk2 (MAPK1)).

In one particular embodiment, the present invention comprises determining the expression level (e.g., total amount) and/or activation level (e.g., level of phosphorylation or complex formation) of at least one, two, three, four, five, six, seven, eight, nine, or ten of the following analytes: HER1, HER2, HER3, cMET, cKIT, IGF-1R, PI3K (e.g., PIK3CA and/or PIK3R1), AKT, ERK (e.g., ERK1 (MAPK3) and/or ERK2 (MAPK1)), and SHC.

In some embodiments, the activation level corresponds to a level of phosphorylation of HER1, HER2, HER3, cMET, cKIT, IGF-1R, AKT, ERK, and/or SHC. In certain other embodiments, the activation level corresponds to a level of a PI3K complex. Examples of PI3K complexes include, without limitation, one or more complexes comprising a dimerized receptor tyrosine kinase pair, a PI3K p85 subunit (e.g., PIK3R1), and a PI3K p110 subunit (e.g., an α or β subunit such as PIK3CA or PIK3CB); see, for example, U.S. Provisional Application No. 61/530,621, filed Sep. 2, 2011, the disclosure of which is herein incorporated by reference in its entirety for all purposes.

In certain embodiments, the present invention further comprises determining the expression level (e.g., total amount) and/or activation level (e.g., level of phosphorylation or complex formation) of one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes in a cellular extract. In some embodiments, the one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes comprises one or more signal transduction molecules selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

In particular embodiments, the present invention further comprises determining the expression level (e.g., total amount) and/or activation level (e.g., level of phosphorylation or complex formation) of one or any combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more of the following additional analytes in a cellular extract: HER4, MEK, PTEN, SGK3, 4E-BP1, PDK1, PDK2, GSK-3β, Raf, SRC, NFkB-IkB, mTOR, EPH-A, EPH-B, EPH-C, EPH-D, FLT-3, TIE-1, TIE-2, c-FMS, Abl, FTL 3, RET, FGFR1, FGFR2, FGFR3, FGFR4, ER, PR, NCOR, AIB1, RON, PIP2, PIP3, p27, protein tyrosine phosphatases (e.g., PTP1B, PTPN13, BDP1, etc.), receptor dimers, and combinations thereof.

Total expression and activation (e.g., phosphorylation) levels of analytes such as signal transduction molecules can be determined using any of a variety of techniques. In certain embodiments, the expression and/or activation (e.g., phosphorylation) level and/or status of analytes such as signal transduction molecules in samples such as cellular extracts of cancer cells is detected with an immunoassay such as a single detection assay or a proximity dual detection assay (e.g., CEER™) as described herein.

In certain embodiments, determining the expression (e.g., total) levels of the one or more analytes comprises:
(i) incubating (e.g., contacting) a cellular extract produced from the cell with one or a plurality of dilution series of capture antibodies (e.g., capture antibodies specific for one or more analytes) to form a plurality of captured analytes, wherein the capture antibodies are restrained on a solid support (e.g., to transform the analytes present in the cellular extract into complexes of captured analytes comprising the analytes and capture antibodies);

(ii) incubating (e.g., contacting) the plurality of captured analytes with detection antibodies comprising one or a plurality of first and second activation state-independent antibodies specific for the corresponding analytes (e.g., first and second activation state-independent antibodies specific for the one or more analytes) to form a plurality of detectable captured analytes (e.g., to transform the complexes of captured analytes into complexes of detectable captured analytes comprising the captured analytes and detection antibodies), wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(iii) incubating (e.g., contacting) the plurality of detectable captured analytes with a second member of the signal amplification pair to generate an amplified signal; and (iv) detecting the amplified signal generated from the first and second members of the signal amplification pair.

In certain other embodiments, determining the expression (e.g., total) levels of the one or more analytes that are truncated receptors (e.g., p95HER2) comprises:

(i) incubating (e.g., contacting) a cellular extract produced from the cell with a plurality of beads specific for an extracellular domain (ECD) binding region of a full-length receptor (e.g., full-length HER2);

(ii) removing the plurality of beads from the cellular extract, thereby removing the full-length receptor (e.g., full-length HER2) to form a cellular extract devoid of the full-length receptor (e.g., full-length HER2) (e.g., to transform the cellular extract into a cellular extract devoid of a specific full-length receptor or family of full-length receptors);

(iii) incubating (e.g., contacting) the cellular extract devoid of the full-length receptor (e.g., full-length HER2) with one or a plurality of capture antibodies specific for an intracellular domain (ICD) binding region of the full-length receptor (e.g., full-length HER2) to form a plurality of captured truncated receptors, wherein the capture antibodies are restrained on a solid support (e.g., to transform the truncated receptors present in a full-length receptor-depleted cellular extract into complexes of truncated receptors and capture antibodies);

(iv) incubating the plurality of captured truncated receptors with detection antibodies comprising one or a plurality of first and second activation state-independent antibodies specific for an ICD binding region of the full-length receptor (e.g., full-length HER2) to form a plurality of detectable captured truncated receptors (e.g., to transform the complexes of captured truncated receptors into complexes of detectable captured truncated receptors comprising the captured truncated receptors and detection antibodies), wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(v) incubating (e.g., contacting) the plurality of detectable captured truncated receptors with a second member of the signal amplification pair to generate an amplified signal; and (vi) detecting the amplified signal generated from the first and second members of the signal amplification pair.

The first activation state-independent antibodies may be directly labeled with the facilitating moiety or indirectly labeled with the facilitating moiety, e.g., via hybridization between an oligonucleotide conjugated to the first activation state-independent antibodies and a complementary oligonucleotide conjugated to the facilitating moiety. Similarly, the second activation state-independent antibodies may be directly labeled with the first member of the signal amplification pair or indirectly labeled with the first member of the signal amplification pair, e.g., via binding between a first member of a binding pair conjugated to the second activation state-independent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the first activation state-independent antibodies can be conjugated to a sulfhydryl-activated dextran molecule as described in, e.g., Examples 16-17 of PCT Publication No. WO2009/108637, the disclosure of which is herein incorporated by reference in its entirety for all purposes. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the second activation state-independent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

The truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95HER2 and the corresponding full-length receptor is HER2. However, one skilled in the art will appreciate that the methods described herein for detecting truncated proteins can be applied to a number of different proteins including, but not limited to, the EGFR VIII mutant (implicated in glioblastoma, colorectal cancer, etc.), other truncated receptor tyrosine kinases, caspases, and the like. Example 12 of PCT Publication No. WO2009/108637, the disclosure of which is herein incorporated by reference in its entirety for all purposes, provides an exemplary embodiment of the assay methods of the present invention for detecting truncated receptors such as p95HER2 in cells using a multiplex, high-throughput, proximity dual detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor (e.g., full-length HER2).

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto an array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.). Exemplary methods for constructing antibody arrays suitable for use in the invention are described, e.g., in PCT Publication No. WO2009/108637, the disclosure of which is herein incorporated by reference in its entirety for all purposes.

In further embodiments, determining the activation levels of the one or more analytes comprises detecting a phosphorylation level of the one or more analytes in the cellular extract with antibodies specific for the phosphorylated form of each of the analytes to be detected.

Phosphorylation levels and/or status can be determined using any of a variety of techniques. For example, it is well known in the art that phosphorylated proteins can be detected via immunoassays using antibodies that specifically recognize the phosphorylated form of the protein (see, e.g., Lin et al, *Br. J. Cancer,* 93:1372-1381 (2005)). Immunoassays generally include immunoblotting (e.g., Western blotting), RIA, and ELISA. More specific types of immunoassays include antigen capture/antigen competition, antibody capture/antigen competition, two-antibody sandwiches, antibody capture/antibody excess, and antibody capture/ antigen excess. Methods of making antibodies are described herein and in Harlow and Lane, Antibodies: A Laboratory Manual, 1988, Cold Spring Harbor Laboratory Press, Cold Spring Harbor, N.Y., USA. Phospho-specific antibodies can be made de novo or obtained from commercial or noncommercial sources. Phosphorylation levels and/or status can also be determined by metabolically labeling cells with radioactive phosphate in the form of $[\gamma\text{-}^{32}P]ATP$ or $[\gamma\text{-}^{33}P]$ ATP. Phosphorylated proteins become radioactive and hence traceable and quantifiable through scintillation counting, radiography, and the like (see, e.g., Wang et al., *J. Biol. Chem.,* 253:7605-7608 (1978)). For example, metabolically labeled proteins can be extracted from cells, separated by gel electrophoresis, transferred to a membrane, probed with an antibody specific for a particular analyte and subjected to autoradiography to detect $^{32}P$ or $^{33}P$. Alternatively, the gel can be subjected to autoradiography prior to membrane transference and antibody probing.

In particular embodiments, the activation (e.g., phosphorylation) level and/or status of each of the one or more analytes in a sample is detected with an immunoassay such as a single detection assay or a proximity dual detection assay (e.g., a Collaborative Enzyme Enhanced Reactive Immunoassay (CEER)) as described herein.

In certain embodiments, determining the activation (e.g., phosphorylation) level of the one or more analytes comprises:
(i) incubating (e.g., contacting) a cellular extract produced from the cell with a dilution series of capture antibodies (e.g., capture antibodies specific for one or more analytes) to form a plurality of captured analytes, wherein the capture antibodies are restrained on a solid support (e.g., to transform the analytes present in the cellular extract into complexes of captured analytes comprising the analytes and capture antibodies);
(ii) incubating (e.g., contacting) the plurality of captured analytes with detection antibodies comprising activation state-independent antibodies specific for the corresponding analytes (e.g., activation state-independent antibodies specific for the one or more analytes) and activation state-dependent antibodies specific for the corresponding analytes (e.g., activation state-dependent antibodies specific for the one or more analytes) to form a plurality of detectable captured analytes (e.g., to transform the complexes of captured analytes into complexes of detectable captured analytes comprising the captured analytes and detection antibodies),
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(iii) incubating (e.g., contacting) the plurality of detectable captured analytes with a second member of the signal amplification pair to generate an amplified signal; and
(iv) detecting the amplified signal generated from the first and second members of the signal amplification pair.

In certain other embodiments, determining the activation (e.g., phosphorylation) level of the one or more analytes that are truncated receptors (e.g., p95HER2) comprises:
(i) incubating (e.g., contacting) a cellular extract produced from the cell with a plurality of beads specific for an extracellular domain (ECD) binding region of a full-length receptor (e.g., full-length HER2);
(ii) removing the plurality of beads from the cellular extract, thereby removing the full-length receptor (e.g., full-length HER2) to form a cellular extract devoid of the full-length receptor (e.g., full-length HER2) (e.g., to transform the cellular extract into a cellular extract devoid of a specific full-length receptor or family of full-length receptors);

(iii) incubating (e.g., contacting) the cellular extract devoid of the full-length receptor (e.g., full-length HER2) with a plurality of capture antibodies specific for an intracellular domain (ICD) binding region of the full-length receptor (e.g., full-length HER2) to form a plurality of captured truncated receptors, wherein the capture antibodies are restrained on a solid support (e.g., to transform the truncated receptors present in a full-length receptor-depleted cellular extract into complexes of truncated receptors and capture antibodies);

(iv) incubating (e.g., contacting) the plurality of captured truncated receptors with detection antibodies comprising activation state-independent antibodies and activation state-dependent antibodies specific for an ICD binding region of the full-length receptor (e.g., full-length HER2) to form a plurality of detectable captured truncated receptors (e.g., to transform the complexes of captured truncated receptors into complexes of detectable captured truncated receptors comprising the captured truncated receptors and detection antibodies), wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(v) incubating (e.g., contacting) the plurality of detectable captured truncated receptors with a second member of the signal amplification pair to generate an amplified signal; and (vi) detecting the amplified signal generated from the first and second members of the signal amplification pair.

The activation state-independent antibodies may be directly labeled with the facilitating moiety or indirectly labeled with the facilitating moiety, e.g., via hybridization between an oligonucleotide conjugated to the activation state-independent antibodies and a complementary oligonucleotide conjugated to the facilitating moiety. Similarly, the activation state-dependent antibodies may be directly labeled with the first member of the signal amplification pair or indirectly labeled with the first member of the signal amplification pair, e.g., via binding between a first member of a binding pair conjugated to the activation state-dependent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the activation state-independent antibodies can be conjugated to a sulfhydryl-activated dextran molecule as described in, e.g., Examples 16-17 of PCT Publication No. WO2009/108637, the disclosure of which is herein incorporated by reference in its entirety for all purposes. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the activation state-dependent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

The truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95HER2 and the corresponding full-length receptor is HER2. However, one skilled in the art will appreciate that the methods described herein for detecting truncated proteins can be applied to a number of different proteins including, but not limited to, the EGFR VIII mutant (implicated in glioblastoma, colorectal cancer, etc.), other truncated receptor tyrosine kinases, caspases, and the like. Example 12 of PCT Publication No. WO2009/108637, the disclosure of which is herein incorporated by reference in its entirety for all purposes, provides an exemplary embodiment of the assay methods of the present invention for detecting truncated receptors such as p95HER2 in cells using a multiplex, high-throughput, proximity dual detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor (e.g., full-length HER2).

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto an array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.). Exemplary methods for constructing antibody arrays suitable for use in the invention are described, e.g., in PCT Publication No. WO2009/108637, the disclosure of which is herein incorporated by reference in its entirety for all purposes.

IV. Single Detection Assays

In some embodiments, the assay for detecting the expression and/or activation level of one or more analytes of interest in a cellular extract of cells such as tumor cells is a multiplex, high-throughput two-antibody assay having superior dynamic range. As a non-limiting example, the two antibodies used in the assay can comprise: (1) a capture antibody specific for a particular analyte of interest; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody comprises an activation state-independent antibody, which detects the total amount of the analyte in the cellular extract. The activation state-independent antibody is generally capable of detecting both the activated and non-activated forms of the analyte.

In one particular embodiment, the two-antibody assay for detecting the expression or activation level of an analyte of interest comprises:
(i) incubating the cellular extract with one or a plurality of dilution series of capture antibodies to form a plurality of captured analytes;
(ii) incubating the plurality of captured analytes with detection antibodies specific for the corresponding analytes to form a plurality of detectable captured analytes, wherein the detection antibodies comprise activation state-dependent antibodies for detecting the activation (e.g., phosphorylation) level of the analyte or activation state-independent antibodies for detecting the expression level (e.g., total amount) of the analyte;
(iii) incubating the plurality of detectable captured analytes with first and second members of a signal amplification pair to generate an amplified signal; and
(iv) detecting the amplified signal generated from the first and second members of the signal amplification pair.

The two-antibody assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies and detection antibodies are preferably selected to minimize competition between them with respect to analyte binding (i.e., both capture and detection antibodies can simultaneously bind their corresponding signal transduction molecules).

In one embodiment, the detection antibodies comprise a first member of a binding pair (e.g., biotin) and the first member of the signal amplification pair comprises a second member of the binding pair (e.g., streptavidin). The binding pair members can be coupled directly or indirectly to the detection antibodies or to the first member of the signal amplification pair using methods well-known in the art. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

An exemplary protocol for performing the two-antibody assays described herein is provided in Example 3 of PCT Publication No. WO2009/108637, the disclosure of which is herein incorporated by reference in its entirety for all purposes.

In another embodiment of a two-antibody approach, the present invention provides a method for detecting the expression or activation level of a truncated receptor, the method comprising:
(i) incubating the cellular extract with a plurality of beads specific for an extracellular domain (ECD) binding region of a full-length receptor;
(ii) removing the plurality of beads from the cellular extract, thereby removing the full-length receptor to form a cellular extract devoid of the full-length receptor;
(iii) incubating the cellular extract devoid of the full-length receptor with a dilution series of one or a plurality of capture antibodies specific for an intracellular domain (ICD) binding region of the full-length receptor to form a plurality of captured truncated receptors;
(iv) incubating the plurality of captured truncated receptors with detection antibodies specific for an ICD binding region of the full-length receptor to form a plurality of detectable captured truncated receptors, wherein the detection antibodies comprise activation state-dependent antibodies for detecting the activation (e.g., phosphorylation) level of the truncated receptor or activation state-independent antibodies for detecting the expression level (e.g., total amount) of the truncated receptor;
(v) incubating the plurality of detectable captured truncated receptors with first and second members of a signal amplification pair to generate an amplified signal; and
(vi) detecting an amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

FIG. 14A of PCT Publication No. WO2009/108637, the disclosure of which is herein incorporated by reference in its entirety for all purposes, shows that beads coated with an antibody directed to the extracellular domain (ECD) of a receptor of interest binds the full-length receptor (e.g., HER2), but not the truncated receptor (e.g., p95HER2) to remove any full-length receptor from the assay. FIG. 14B of PCT Publication No. WO2009/108637 shows that the truncated receptor (e.g., p95HER2), once bound to a capture antibody, may then be detected by a detection antibody that is specific for the intracellular domain (ICD) of the full-length receptor (e.g., HER2). The detection antibody may be directly conjugated to horseradish peroxidase (HRP). Tyramide signal amplification (TSA) may then be performed to generate a signal to be detected. The expression level or activation state of the truncated receptor (e.g., p95HER2) can be interrogated to determine, e.g., its total concentration or its phosphorylation state, ubiquitination state, and/or complexation state.

In another embodiment, the present invention provides kits for performing the two-antibody assays described above comprising: (a) a dilution series of one or a plurality of capture antibodies restrained on a solid support; and (b) one or a plurality of detection antibodies (e.g., activation state-independent antibodies and/or activation state-dependent antibodies). In some instances, the kits can further contain instructions for methods of using the kit to detect the expression levels and/or activation states of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, wash buffers, etc.

V. Proximity Dual Detection Assays

In some embodiments, the assay for detecting the expression and/or activation level of one or more analytes of interest in a cellular extract of cells such as tumor cells is a multiplex, high-throughput proximity (i.e., three-antibody) assay having superior dynamic range. As a non-limiting example, the three antibodies used in the proximity assay can comprise: (1) a capture antibody specific for a particular analyte of interest; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, e.g., the phosphorylation, ubiquitination, and/or complexation state of the analyte, while the activation state-independent antibody is capable of detecting the total amount (i.e., both the activated and non-activated forms) of the analyte.

In one particular embodiment, the proximity assay for detecting the activation level or status of an analyte of interest comprises:
(i) incubating the cellular extract with one or a plurality of dilution series of capture antibodies to form a plurality of captured analytes;

(ii) incubating the plurality of captured analytes with detection antibodies comprising one or a plurality of activation state-independent antibodies and one or a plurality of activation state-dependent antibodies specific for the corresponding analytes to form a plurality of detectable captured analytes, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(iii) incubating the plurality of detectable captured analytes with a second member of the signal amplification pair to generate an amplified signal; and (iv) detecting the amplified signal generated from the first and second members of the signal amplification pair.

In another particular embodiment, the proximity assay for detecting the activation level or status of an analyte of interest that is a truncated receptor comprises:
(i) incubating the cellular extract with a plurality of beads specific for an extracellular domain (ECD) binding region of a full-length receptor;

(ii) removing the plurality of beads from the cellular extract, thereby removing the full-length receptor to form a cellular extract devoid of the full-length receptor;

(iii) incubating the cellular extract devoid of the full-length receptor with one or a plurality of capture antibodies specific for an intracellular domain (ICD) binding region of the full-length receptor to form a plurality of captured truncated receptors;

(iv) incubating the plurality of captured truncated receptors with detection antibodies comprising one or a plurality of activation state-independent antibodies and one or a plurality of activation state-dependent antibodies specific for an ICD binding region of the full-length receptor to form a plurality of detectable captured truncated receptors, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(v) incubating the plurality of detectable captured truncated receptors with a second member of the signal amplification pair to generate an amplified signal; and (vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the activation state-dependent antibodies can be labeled with a facilitating moiety and the activation state-independent antibodies can be labeled with a first member of a signal amplification pair.

As another non-limiting example, the three antibodies used in the proximity assay can comprise: (1) a capture antibody specific for a particular analyte of interest; (2) a first detection antibody which detects the total amount of the analyte (i.e., a first activation state-independent antibody); and (3) a second detection antibody which detects the total amount of the analyte (i.e., a second activation state-independent antibody). In preferred embodiments, the first and second activation state-independent antibodies recognize different (e.g., distinct) epitopes on the analyte.

In one particular embodiment, the proximity assay for detecting the expression level of an analyte of interest comprises:
  (i) incubating the cellular extract with one or a plurality of dilution series of capture antibodies to form a plurality of captured analytes;
  (ii) incubating the plurality of captured analytes with detection antibodies comprising one or a plurality of first and second activation state-independent antibodies specific for the corresponding analytes to form a plurality of detectable captured analytes,
  wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;
  (iii) incubating the plurality of detectable captured analytes with a second member of the signal amplification pair to generate an amplified signal; and
  (iv) detecting the amplified signal generated from the first and second members of the signal amplification pair.

In another particular embodiment, the proximity assay for detecting the expression level of an analyte of interest that is a truncated receptor comprises:
  (i) incubating the cellular extract with a plurality of beads specific for an extracellular domain (ECD) binding region of a full-length receptor;
  (ii) removing the plurality of beads from the cellular extract, thereby removing the full-length receptor to form a cellular extract devoid of the full-length receptor;
  (iii) incubating the cellular extract devoid of the full-length receptor with one or a plurality of capture antibodies specific for an intracellular domain (ICD) binding region of the full-length receptor to form a plurality of captured truncated receptors;
  (iv) incubating the plurality of captured truncated receptors with detection antibodies comprising one or a plurality of first and second activation state-independent antibodies specific for an ICD binding region of the full-length receptor to form a plurality of detectable captured truncated receptors,
  wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;
  (v) incubating the plurality of detectable captured truncated receptors with a second member of the signal amplification pair to generate an amplified signal; and
  (vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the first activation state-independent antibodies can be labeled with a first member of a signal amplification pair and the second activation state-independent antibodies can be labeled with a facilitating moiety.

The proximity assays described herein are typically antibody-based arrays which comprise one or a plurality of different capture antibodies at a range of capture antibody concentrations that are coupled to the surface of a solid support in different addressable locations. Examples of suitable solid supports for use in the present invention are described above.

The capture antibodies, activation state-independent antibodies, and activation state-dependent antibodies are preferably selected to minimize competition between them with respect to analyte binding (i.e., all antibodies can simultaneously bind their corresponding signal transduction molecules).

In some embodiments, activation state-independent antibodies for detecting activation levels of one or more of the analytes or, alternatively, first activation state-independent antibodies for detecting expression levels of one or more of the analytes further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor® 647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well-known in the art.

In certain instances, activation state-independent antibodies for detecting activation levels of one or more of the analytes or, alternatively, first activation state-independent antibodies for detecting expression levels of one or more of the analytes are directly labeled with the facilitating moiety. The facilitating moiety can be coupled to activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, activation state-independent antibodies for detecting activation levels of one or more of the analytes or, alternatively, first activation state-independent antibodies for detecting expression levels of one or more of the analytes are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is between 1-10° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-reactivity between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, activation state-dependent antibodies for detecting activation levels of one or more of the analytes or, alternatively, second activation state-independent antibodies for detecting expression levels of one or more of the analytes are directly labeled with the first member of the signal amplification pair. The signal amplification pair member can be coupled to activation state-dependent antibodies to detect activation levels or second activation state-independent antibodies to detect expression levels using methods well-known in the art. In certain other instances, activation state-dependent antibodies or second activation state-independent antibodies are indirectly labeled with the first member of the signal amplification pair via binding between a first member of a binding pair conjugated to the activation state-dependent antibodies or second activation state-independent antibodies and a second member of the binding pair conjugated to the first member of the signal amplification pair. The binding pair members (e.g., biotin/streptavidin) can be coupled to the signal amplification pair member or to the activation state-dependent antibodies or second activation state-independent antibodies using methods well-known in the art. Examples of signal amplification pair members include, but are not limited to, peroxidases such as horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocyanate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, thioether-, and selenoether-protecting groups. Additional photosensitizers and protected hapten molecules suitable for use in the proximity assays of the present invention are described in U.S. Pat. No. 5,807,675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, β-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

An exemplary protocol for performing the proximity assays described herein is provided in Example 4 of PCT Publication No. WO2009/108637, the disclosure of which is herein incorporated by reference in its entirety for all purposes.

In another embodiment, the present invention provides kits for performing the proximity assays described above comprising: (a) a dilution series of one or a plurality of capture antibodies restrained on a solid support; and (b) one or a plurality of detection antibodies (e.g., a combination of activation state-independent antibodies and activation state-dependent antibodies for detecting activation levels and/or a combination of first and second activation state-independent antibodies for detecting expression levels). In some instances, the kits can further contain instructions for methods of using the kit to detect the expression and/or activation status of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, substrates for the facilitating moiety, wash buffers, etc.

VI. Methods of Genotyping

A variety of means can be used to genotype an individual at a polymorphic site in an oncogene such as the KRAS, BRAF, PIK3CA, and/or EGFR gene to determine whether a sample (e.g., a nucleic acid sample) contains a specific variant allele (e.g., somatic mutation) or haplotype. For example, enzymatic amplification of nucleic acid from an individual can be conveniently used to obtain nucleic acid for subsequent analysis. The presence or absence of a specific variant allele (e.g., somatic mutation) or haplotype in one or more oncogenes of interest can also be determined directly from the individual's nucleic acid without enzymatic amplification. In certain embodiments, an individual is genotyped at one, two, three, four, five, or more polymorphic sites such as a single nucleotide polymorphism (SNP) in one or more oncogenes of interest.

Genotyping of nucleic acid from an individual, whether amplified or not, can be performed using any of various techniques. Useful techniques include, without limitation, assays such as polymerase chain reaction (PCR) based analysis assays, sequence analysis assays, electrophoretic analysis assays, restriction length polymorphism analysis assays, hybridization analysis assays, allele-specific hybridization, oligonucleotide ligation allele-specific elongation/ligation, allele-specific amplification, single-base extension, molecular inversion probe, invasive cleavage, selective termination, restriction length polymorphism, sequencing, single strand conformation polymorphism (SSCP), single strand chain polymorphism, mismatch-cleaving, and denaturing gradient gel electrophoresis, all of which can be used alone or in combination. As used herein, the term "nucleic acid" includes a polynucleotide such as a single- or double-stranded DNA or RNA molecule including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

In particular embodiments, the presence or absence of a variant allele (e.g., somatic mutation) in one or more oncogenes of interest is determined using a genotyping assay as described in U.S. Provisional Application No. 61/525,137, filed Aug. 18, 2011, and U.S. Provisional Application No. 61/588,151, filed Jan. 18, 2012, the disclosures of which are herein incorporated by reference in their entirety for all purposes.

Material containing nucleic acid is routinely obtained from individuals. Such material is any biological matter from which nucleic acid can be prepared. As non-limiting examples, material can be whole blood, serum, plasma, saliva, cheek swab, sputum, or other bodily fluid or tissue that contains nucleic acid. In one embodiment, a method of the present invention is practiced with whole blood, which can be obtained readily by non-invasive means and used to prepare genomic DNA. In another embodiment, genotyping involves amplification of an individual's nucleic acid using the polymerase chain reaction (PCR). Use of PCR for the amplification of nucleic acids is well known in the art (see, e.g., Mullis et al. (Eds.), *The Polymerase Chain Reaction*, Birkhäuser, Boston, (1994)). In yet another embodiment, PCR amplification is performed using one or more fluorescently labeled primers. In a further embodiment, PCR amplification is performed using one or more labeled or unlabeled primers that contain a DNA minor groove binder.

Any of a variety of different primers can be used to amplify an individual's nucleic acid by PCR in order to determine the presence or absence of a variant allele (e.g., somatic mutation) in a method of the invention. As understood by one skilled in the art, primers for PCR analysis can be designed based on the sequence flanking the polymorphic site(s) of interest in the gene of interest. As a non-limiting example, a sequence primer can contain from about 15 to about 30 nucleotides of a sequence upstream or downstream of the polymorphic site of interest in the gene of interest. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site to thereby determine the presence or absence of a particular variant allele (e.g., somatic mutation) or haplotype in the gene of interest. In a Taqman® allelic discrimination assay, a specific fluorescent dye-labeled probe for each allele is constructed. The probes contain different fluorescent reporter dyes such as FAM and VIC™ to differentiate amplification of each allele. In addition, each probe has a quencher dye at one end which quenches fluorescence by fluorescence resonance energy transfer. During PCR, each probe anneals specifically to complementary sequences in the nucleic acid from the individual. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor groove binder (MGB) group to a DNA probe as described, e.g., in Kutyavin et al., *Nuc. Acids Research* 28:655-661 (2000). Minor groove binders include, but are not limited to, compounds such as dihydrocyclopyrroloindole tripeptide (DPI3).

Sequence analysis can also be useful for genotyping an individual according to the methods described herein to determine the presence or absence of a particular variant allele (e.g., somatic mutation) or haplotype in the gene of interest. As is known by those skilled in the art, a variant allele of interest can be detected by sequence analysis using the appropriate primers, which are designed based on the sequence flanking the polymorphic site of interest in the gene of interest. For example, a variant allele in a gene of interest can be detected by sequence analysis using primers designed by one of skill in the art. Additional or alternative sequence primers can contain from about 15 to about 30 nucleotides of a sequence that corresponds to a sequence about 40 to about 400 base pairs upstream or downstream of the polymorphic site of interest in the gene of interest. Such primers are generally designed to have sufficient guanine and cytosine content to attain a high melting temperature which allows for a stable annealing step in the sequencing reaction.

The term "sequence analysis" includes any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (see, Sears et al., *Biotechniques* 13:626-633 (1992)); solid-phase sequencing (see, Zimmerman et al., *Methods Mol. Cell Biol.* 3:39-42 (1992); and sequencing with mass spectrometry, such as matrix-assisted laser desorption/ionization time-of-flight mass spectrometry (see, MALDI-TOF MS; Fu et al., *Nature Biotech.* 16:381-384 (1998)). The term sequence analysis further includes, but is not limited to, sequencing by hybridization (SBH), which relies on an array of all possible short oligonucleotides to identify a segment of sequence (see, Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein.

Electrophoretic analysis also can be useful in genotyping an individual according to the methods of the present invention to determine the presence or absence of a particular variant allele (e.g., somatic mutation) or haplotype in the gene of interest. "Electrophoretic analysis" as used herein in reference to one or more nucleic acids such as amplified fragments includes a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis can also be useful for genotyping an individual according to the methods of the present invention to determine the presence or absence of a particular variant allele (e.g., somatic mutation) or haplotype in the gene of interest (see, Jarcho et al. in Dracopoli et al., *Current Protocols in Human Genetics* pages 2.7.1-2.7.5, John Wiley & Sons, New York; Innis et al., (Ed.), *PCR Protocols*, San Diego: Academic Press, Inc. (1990)). As used herein, "restriction fragment length polymorphism analysis" includes any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

In addition, allele-specific oligonucleotide hybridization can be useful for genotyping an individual in the methods described herein to determine the presence or absence of a particular variant allele (e.g., somatic mutation) or haplotype in the gene of interest. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping in the methods of the present invention to determine the presence or absence of a particular variant allele (e.g., somatic mutation) or haplotype in the gene of interest. HMA is useful for detecting the presence of a variant allele since a DNA duplex carrying a mismatch has reduced mobility in a polyacrylamide gel compared to the mobility of a perfectly base-paired duplex (see, Delwart et al., *Science*, 262:1257-1261 (1993); White et al., *Genomics*, 12:301-306 (1992)).

The technique of single strand conformational polymorphism (SSCP) can also be useful for genotyping in the methods described herein to determine the presence or absence of a particular variant allele (e.g., somatic mutation) or haplotype in the gene of interest (see, Hayashi, *Methods Applic.*, 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) can also be useful in the methods of the invention to determine the presence or absence of a particular variant allele (e.g., somatic mutation) or haplotype in the gene of interest. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (see, Sheffield et al., "Identifying DNA Polymorphisms by Denaturing Gradient Gel Electrophoresis" in Innis et al., supra, 1990).

Other molecular methods useful for genotyping an individual are known in the art and useful in the methods of the present invention. Such well-known genotyping approaches include, without limitation, automated sequencing and RNase mismatch techniques (see, Winter et al., *Proc. Natl. Acad. Sci.*, 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple variant alleles can be detected in individual reactions or in a single reaction (a "multiplex" assay).

VII. Production of Antibodies

The generation and selection of antibodies not already commercially available for analyzing the levels of expression and activation of signal transduction molecules in tumor cells in accordance with the immunoassays of the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); *Solid Phase Peptide Synthesis*, Greg B. Fields, ed., *Meth. Enzymol.*, Vol. 289 (1997); Kiso et al., *Chem. Pharm. Bull.*, 38:1192-99 (1990); Mostafavi et al., *Biomed. Pept. Proteins Nucleic Acids*, 1:255-60, (1995); and Fujiwara et al., *Chem. Pharm. Bull.*, 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., *Antibody Engineering: A Practical Approach*, Borrebaeck, Ed., Oxford University Press, Oxford (1995); and Huse et al., *J. Immunol.*, 149:3914-3920 (1992).

Those skilled in the art will recognize that many approaches can be taken in producing antibodies or binding fragments and screening and selecting for affinity and specificity for the various polypeptides of interest, but these approaches do not change the scope of the present invention.

A more detailed description of polyclonal antibodies, monoclonal antibodies, humanized antibodies, human antibodies, bispecific antibodies, fragments thereof, and methods of purifying antibodies is found in PCT Publication No. WO 2010/132723, the disclosure of which is herein incorporated by reference in its entirety for all purposes.

VIII. Methods of Administration

According to the methods of the present invention, the anticancer drugs described herein are administered to a subject by any convenient means known in the art. The methods of the present invention can be used to select a suitable anticancer drug or combination of anticancer drugs for the treatment of a tumor, e.g., a colorectal tumor, in a subject. The methods of the present invention can also be used to identify the response of a tumor, e.g., a colorectal tumor, in a subject to treatment with an anticancer drug or combination of anticancer drugs. In addition, the methods of the present invention can be used to predict the response of a subject having a tumor, e.g., a colorectal tumor, to treatment with an anticancer drug or combination of anticancer drugs. One skilled in the art will appreciate that the anticancer drugs described herein can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the subject is treated with one or more anti-signaling agents, anti-proliferative agents, and/or hormonal therapeutic agents in combination with at least one chemotherapeutic agent. Exemplary monoclonal antibodies, tyrosine kinase inhibitors, anti-proliferative agents, chemotherapeutic agents, hormonal therapeutic agents, radiotherapeutic agents, and vaccines are described above.

In some embodiments, the anticancer drugs described herein can be co-administered with conventional immunotherapeutic agents including, but not limited to, immunostimulants (e.g., *Bacillus* Calmette-Guerin (BCG), levamisole, interleukin-2, alpha-interferon, etc.), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., *REMINGTON'S PHARMACEUTICAL SCIENCES,* 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES,* supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the activation states of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

In certain aspects, the methods described herein can be used in conjunction with panels of gene expression markers that predict the likelihood of colorectal cancer prognosis and/or recurrence in various populations. These gene panels can be useful for identifying individuals who are unlikely to experience recurrence and, thus, unlikely to benefit from adjuvant chemotherapy. The expression panels can be used to identify individuals who can safely avoid adjuvant chemotherapy, without negatively affecting disease-free and overall survival outcomes. Suitable systems include, but are not limited to, Oncotype DX™, which is a 21-gene panel from Genomic Health, Inc.; MammaPrint,® which is a 70-gene panel from Agendia; and a 76-gene panel from Veridex.

In addition, in certain other aspects, the methods described herein can be used in conjunction with panels of gene expression markers that identify the original tumors for cancers of unknown primary (CUP). These gene panels can be useful in identifying patients with metastatic cancer who would benefit from therapy consistent with that given to patients diagnosed initially with colorectal cancer. Suitable systems include, but are not limited to, the Aviara CancerTYPE ID assay, an RT-PCR-based expression assay that measures 92 genes to identify the primary site of origin for 39 tumor types; and the Pathwork® Tissue of Origin Test, which measures the expression of more than 1600 genes on a microarray and compares a tumor's gene expression "signature" against those of 15 known tissue types.

IX. Example

The following example is offered to illustrate, but not to limit, the claimed invention.

Example 1. Molecular Phenotyping of Colorectal Cancers Using CEER: Implications for Patient-Focused Therapeutic Targeting This example illustrates that the ratio of phospho-PI3K (pPI3K) to phospho-HER3 (pHER3) in colorectal cancer (CRC) tumors, regardless of their KRAS status, predicts tumor prognosis and anti-EGFR therapy outcome. As described herein, the best candidates for anti-EGFR therapies may be CRCs with a low pPI3K/pHER3 ratio but a high HER1/cMET ratio. This example also illustrates that pPI3K/pHER1 and pPI3K/pHER2 ratios correlate negatively and significantly with relapse and disease free survival (DFS) in CRC patients. As described herein, pPI3K/pHER1 and pPI3K/pHER2 ratios are higher in CRC samples that have higher pPI3K/pHER3 ratios (e.g., above the reference pPI3K/pHER3 index cut-off).

FIG. 1 shows the CRC cohort study schema. This study included 115 primary CRC tumors and 10 primary/metastatic matched tumor samples. CEER/mutational analysis was performed on the collected samples. HER members (e.g., HER1, HER2, HER3), cMET, IGF1R, PI3K, Shc, AKT, and ERK were analyzed for their expression and/or activation level utilizing the Collaborative Enzyme Enhanced Reactive (CEER) immunoassay. CEER is a highly sensitive and specific proximity assay that relies on the formation of a triple antibody complex surrounding the target protein. Samples were also molecularly characterized for 14 different mutations within the KRAS, BRAF and PIK3CA oncogenes. FIG. 2 illustrates the characteristics of the CRC patients enrolled in this study.

Segregation of CRC tumors based on their KRAS mutational status is currently the best available biomarker for predicting prognosis and therapeutic outcomes. However, CRC patient selection simply based on KRAS mutational status is imperfect. Therefore, an unmet need exists in the CRC field for better biomarkers to predict prognosis and guide selection of therapies for CRC. For example, KRAS wild-type (KRAS-WT) CRC tumors have a mixed prognosis post-surgery for unknown reasons. KRAS-WT CRC tumors have a heterogeneous response post-cetuximab therapy; BRAF mutations are indicated as a reason in some tumors, but these do not explain the majority of cetuximab non-responsive tumors. In addition, KRAS G12 mutant (KRAS-G12mut) CRC tumors typically have a worse prognosis post-surgery for unknown reasons. In particular, KRAS-G12mut CRC tumors typically do not respond to anti-EGFR therapies. Currently, no targeted therapies are available to treat KRAS-G12mut CRC tumors.

Figure 3:
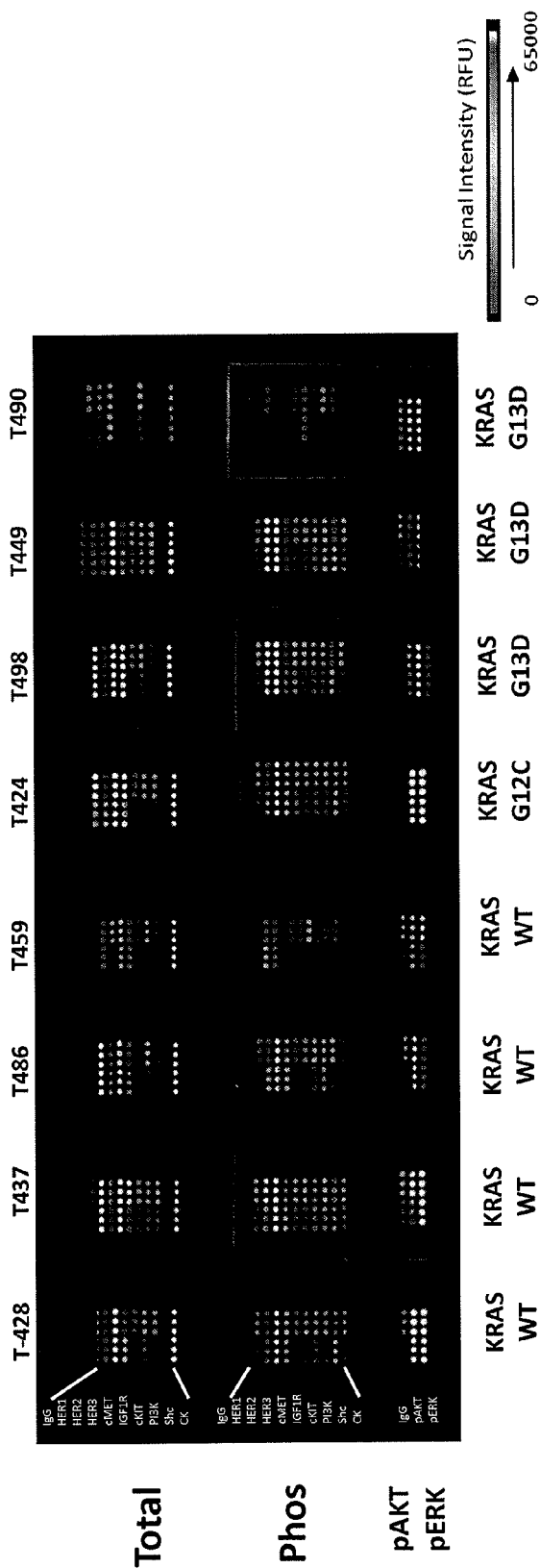
FIG. 3 shows signaling pathway profiling of CRC clinical samples using CEER.

FIG. 3 shows signaling pathway profiling of CRC clinical samples using CEER. Sample examples from eight different patients were analyzed for the expression of total and phosphorylated (phos) HER1, HER2, HER3, cMET, IGF1R, cKIT, PI3K, and Shc. Pan-CK and phosphorylated AKT and ERK were also analyzed. The KRAS mutational status of each sample is indicated.

Figure 4:
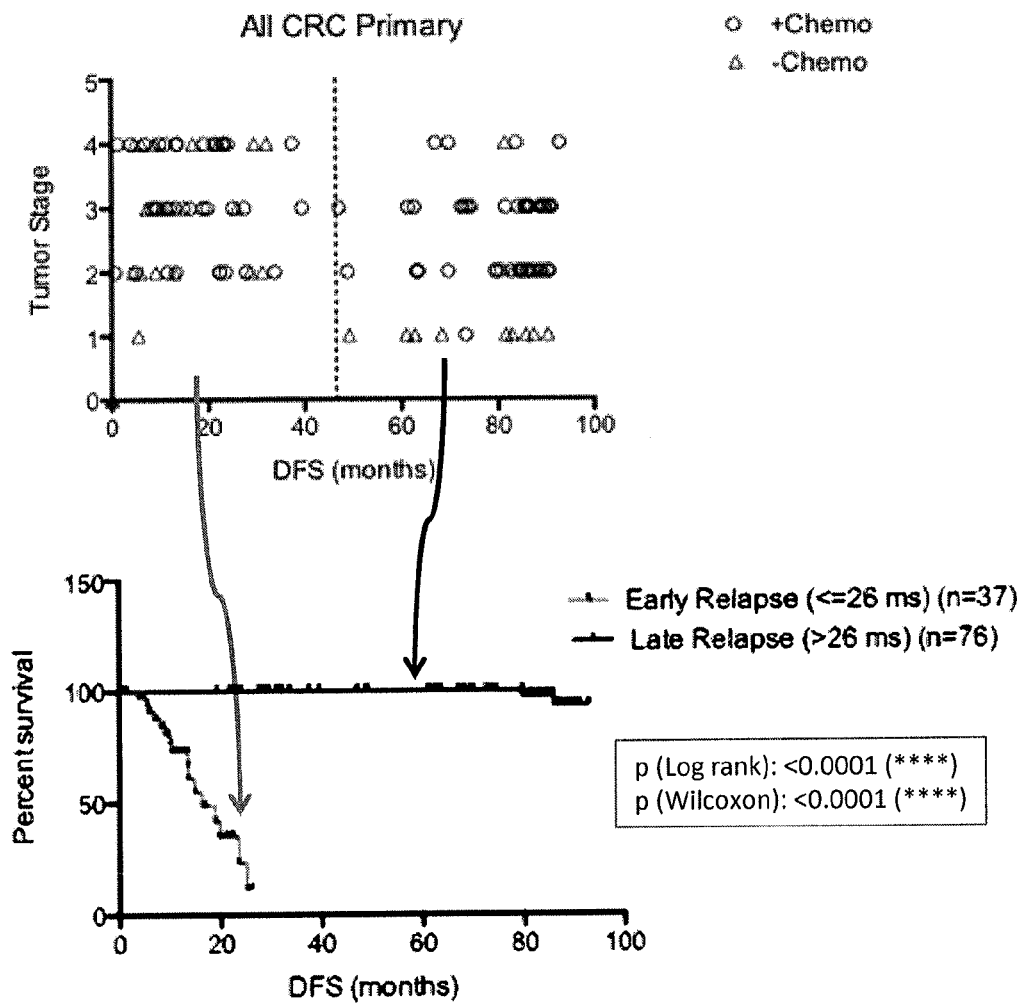
FIG. 4 shows the diversity and heterogeneity in CRC disease-free survival (DFS).
Figure 5:
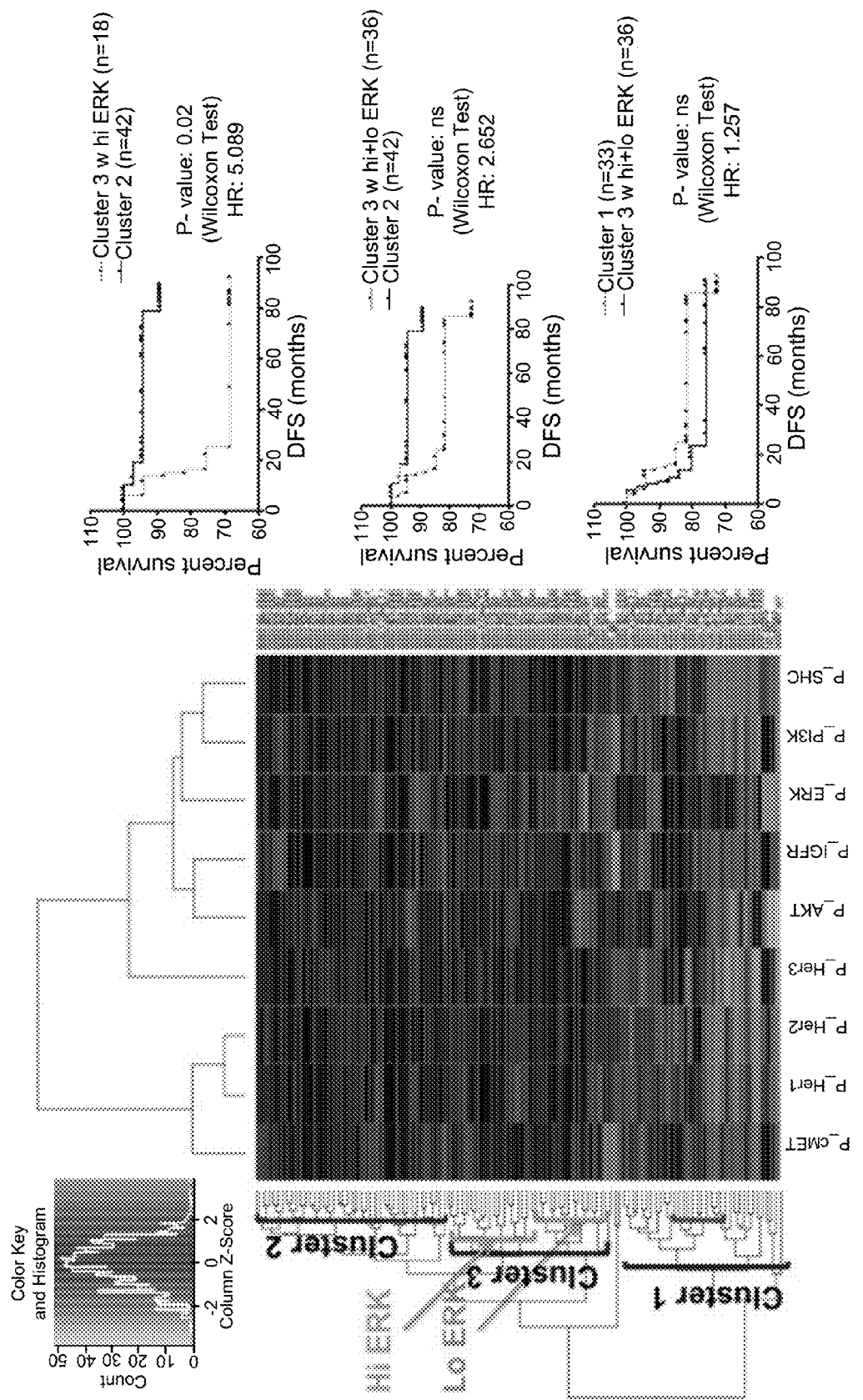
FIG. 5 shows that the diversity in CRC survival correlates with the diversity in signaling pathway signatures.

FIG. 4 shows the diversity and heterogeneity in CRC disease-free survival (DFS). FIG. 5 shows that the diversity in CRC survival correlates with the diversity in signaling pathway signatures. In particular, FIG. 5 shows that disease-free survival differences in CRCs correlate with pathway signatures discovered through the CEER technology.

Figure 6:
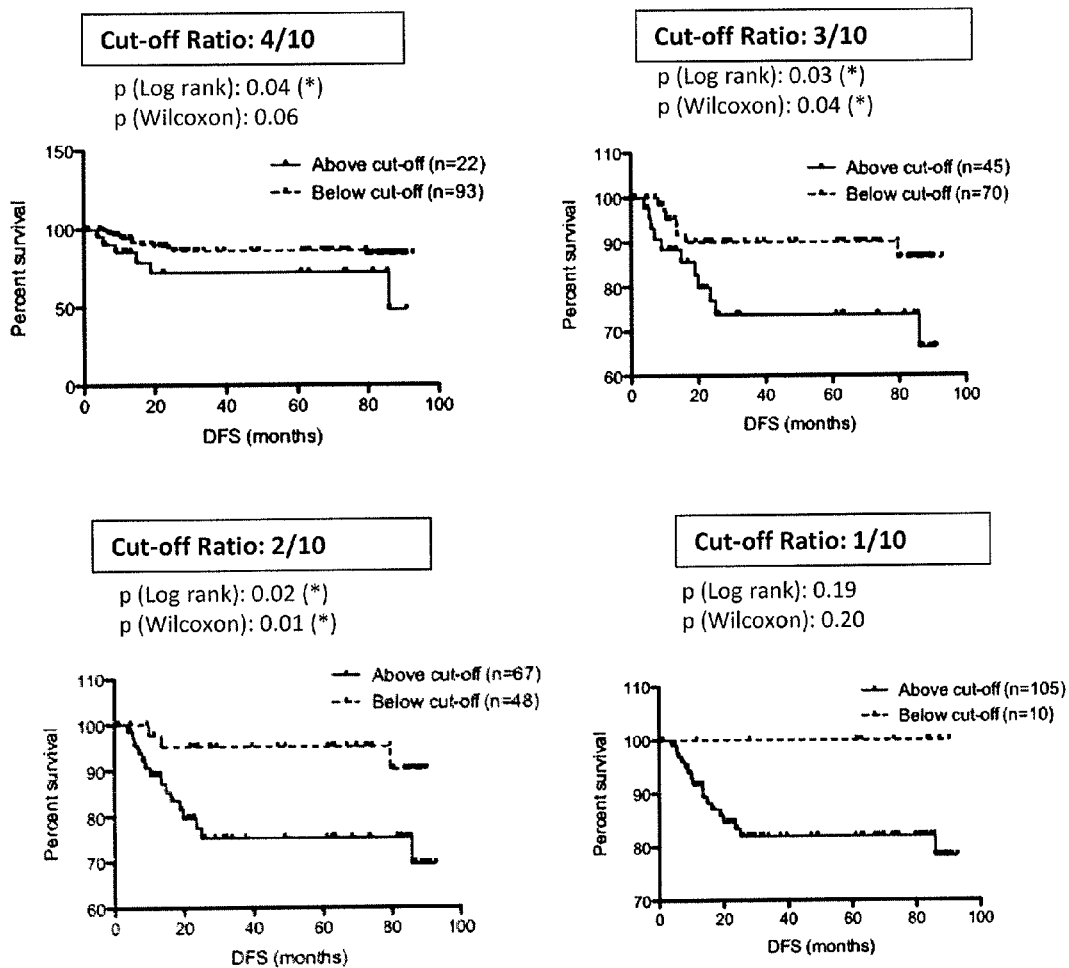
FIG. 6 shows that there is a correlation of decreasing pPI3K/pHER3 index with DFS.
Figure 8:
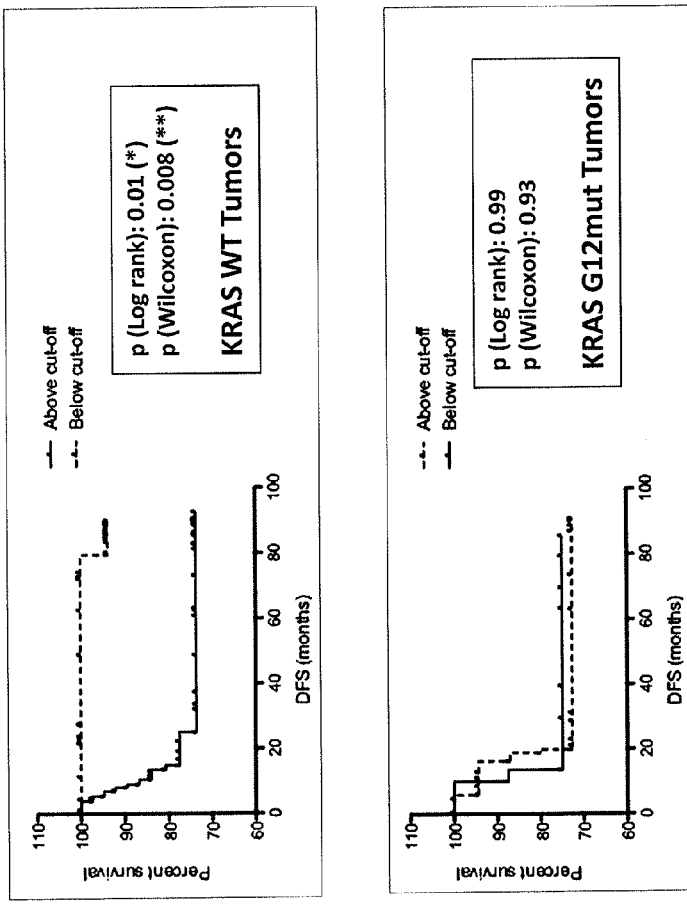
FIG. 8 shows that CRC tumors segregated by the pPI3K/pHER3 index uncovers at least 2 sub-populations within the KRAS wild-type tumors with high and low survival.

FIGS. 6-12 demonstrate that pPI3K/pHER3 is a prognostic marker for CRC. In particular, FIGS. 6-8 show that the pPI3K/pHER3 index or ratio can be utilized to segregate survival differences in CRC patients. As pPI3K level increases with respect to pHER3, there is an increased chance of disease recurrence. FIG. 6 illustrates that there is a correlation of decreasing pPI3K/pHER3 index with DFS. Exemplary cut-off ratios of 1/10 (0.1), 2/10 (0.2), 3/10 (0.3), and 4/10 (0.4) were tested. When a cut-off ratio of 2/10 (0.2) was used for further analysis, poor prognosis of CRC patients with higher pPI3K beyond what could be accounted for by pHER3 was observed. In particular embodiments, CRC patients with a pPI3K/pHER3 ratio <0.2 are candidates for one or more anti-HER therapies, whereas CRC patients with a pPI3K/pHER3 ratio >0.2 are candidates for one or more anti-PI3K therapies. FIG. 7 shows the composition of CRC tumors segregated by pPI3K/pHER3 index. Notably, CRC tumors segregate regardless of tumor stage and KRAS mutational status. FIG. 8 shows that CRC tumors segregated by the pPI3K/pHER3 index uncovers at least 2 sub-populations within the KRAS wild-type tumors with high and low survival. However, KRAS G12mut CRC tumors have a lower survival regardless of their pPI3K/pHER3 index. In other words, KRAS WT tumors clearly segregated into 2 subsets with significantly distinct DFS differences based on their pPI3K/pHER3 index ratio, whereas KRAS G12mut tumors are always aggressive and have a low DFS regardless of their pPI3K/pHER3 ratio. As such, pPI3K/pHER3 expression is a novel prognostic factor for CRC.

Figure 9:
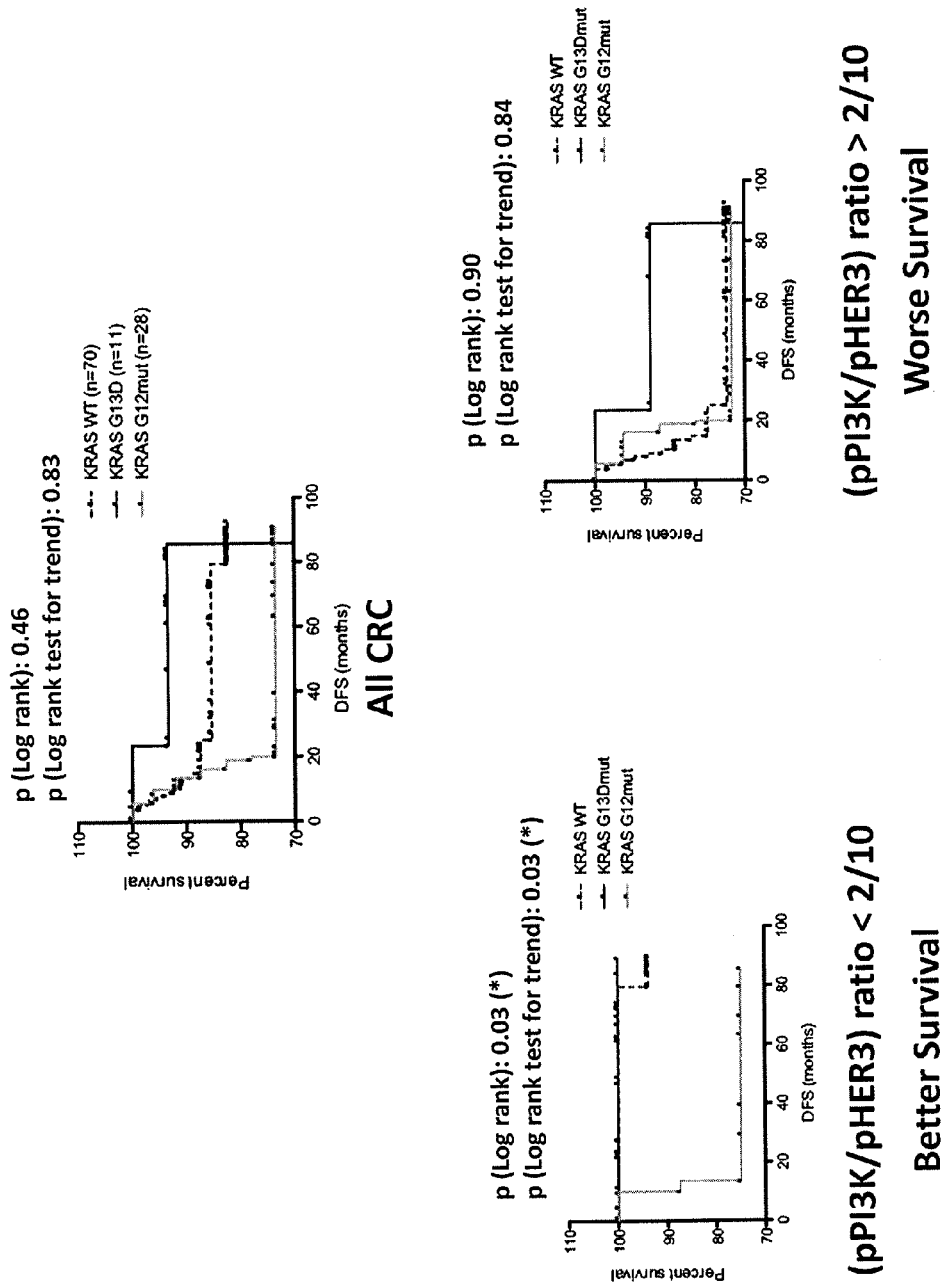
FIG. 9 shows that significant differences in DFS segregation based on KRAS mutational status were observed only in CRC tumors with a low pPI3K/pHER3 index.
Figure 10:
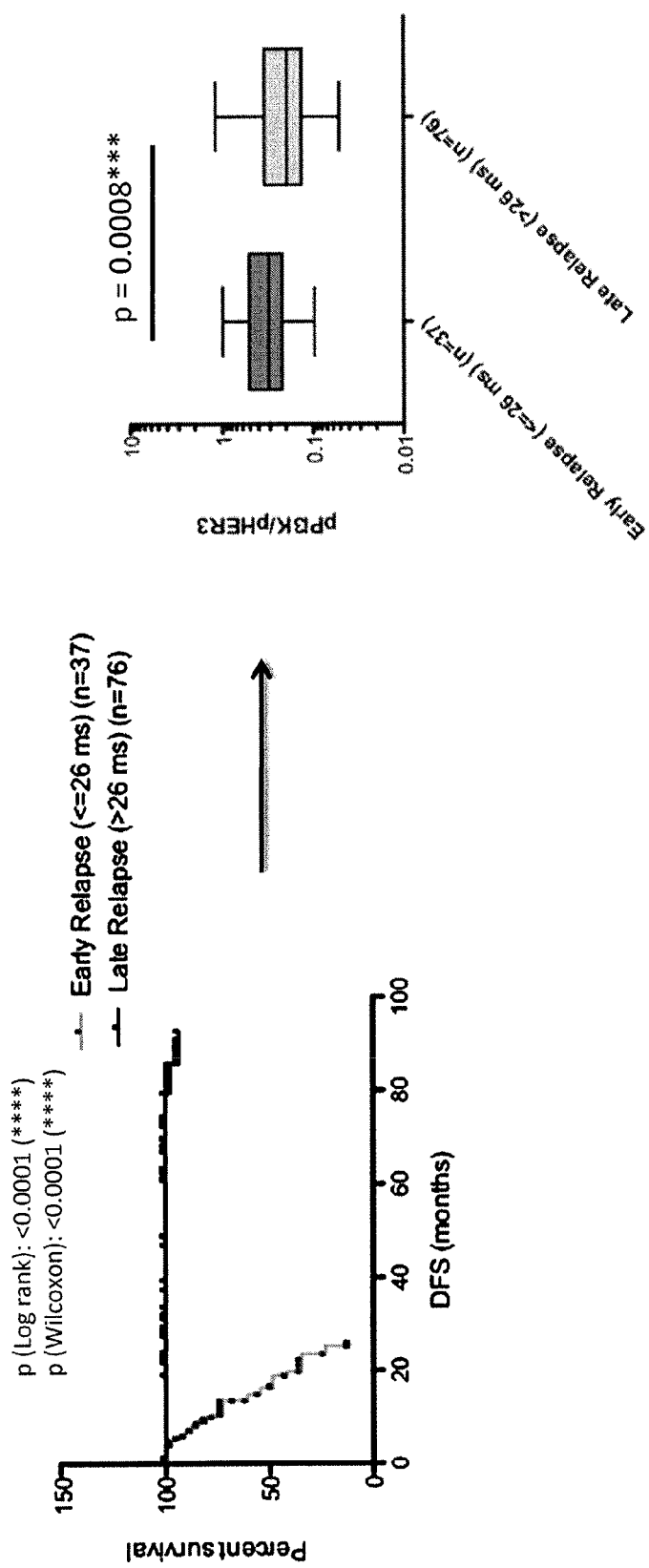
FIG. 10 shows that CRC tumors having a high pPI3K/pHER3 index relapse early, regardless of their KRAS mutational status.
Figure 11:
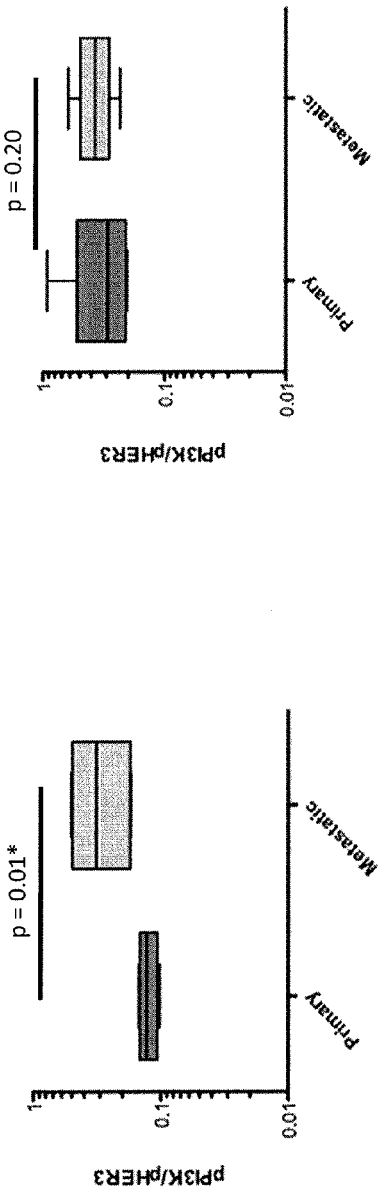
FIG. 11 shows that CRC tumors acquire a high pPI3K/pHER3 index as they metastasize to distant organs.

FIG. 9 illustrates that KRAS mutational status-based prognostic outcome is only applicable in CRCs with a low pPI3K/pHER3 index. In particular, significant differences in DFS segregation based on KRAS mutational status were observed only in CRC tumors with a low pPI3K/pHER3 index. FIG. 10 provides additional evidence that higher pPI3K/pHER3 index correlates with aggressiveness in CRCs. Higher pPI3K signaling correlates with early relapse in CRCs regardless of their KRAS mutational status. In other words, FIG. 10 shows that CRC tumors having a high pPI3K/pHER3 index relapse early, regardless of their KRAS mutational status. FIG. 11 shows that the pPI3K/pHER3 ratio increases (e.g., to above the pPI3K/pHER3 cut-off ratio) as CRCs with low pPI3K signaling metastasize. In particular, CRC tumors acquire a high pPI3K/pHER3 index as they metastasize to distant organs. The therapeutic implication is that targeted therapies need to be adjusted based on their pathway profiling, e.g., anti-HER therapies followed by anti-PI3K therapies.

Figure 12:
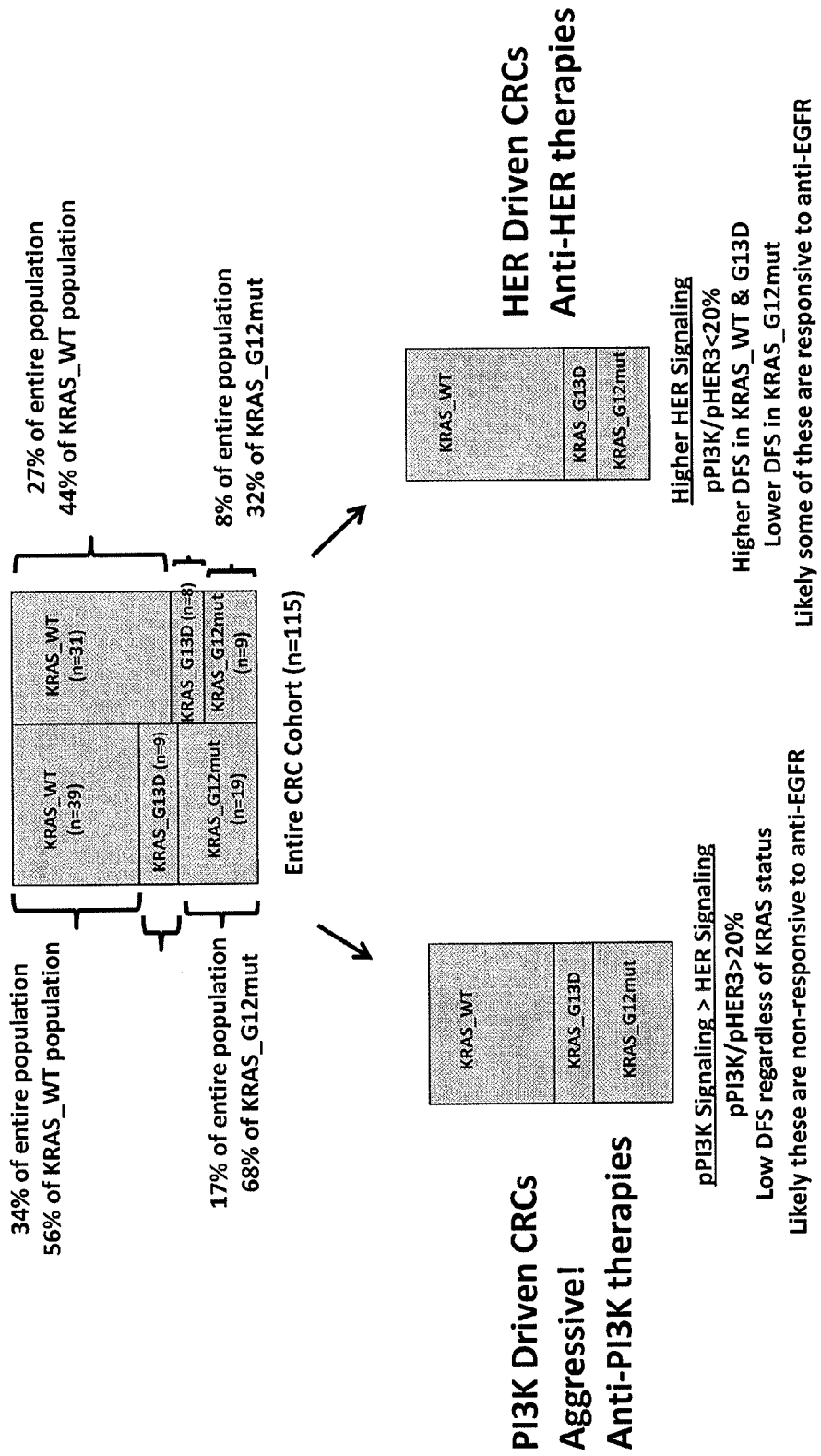
FIG. 12 shows a pictorial summary of the experimental data set forth in FIGS. 6-11.

FIG. 12 provides a pictorial summary of the experimental data set forth in FIGS. 6-11. When the pPI3K/pHER3 index is above the cut-off ratio (e.g., pPI3K/pHER3>20%), pPI3K signaling is greater than HER signaling and the CRC is classified as PI3K-driven. In terms of prognosis, patients with a pPI3K/pHER3 index above the cut-off ratio are predicted to have a low DFS regardless of KRAS mutational status. In terms of CRC therapy selection, patients with a pPI3K/pHER3 index above the cut-off ratio are likely to be non-responsive to anti-EGFR therapies and have a higher likelihood of being responsive to anti-PI3K therapies. When the pPI3K/pHER3 index is below the cut-off ratio (e.g., pPI3K/pHER3<20%), HER signaling is higher and the CRC is classified as HER-driven. In terms of prognosis, patients with a pPI3K/pHER3 index below the cut-off ratio are predicted to have higher DFS when the KRAS status is WT or G13D, but a lower DFS when the KRAS status is KRAS G12mut. In terms of CRC therapy selection, some of the patients with a pPI3K/pHER3 index below the cut-off ratio are likely to be responsive to anti-EGFR therapies.

Figure 13:
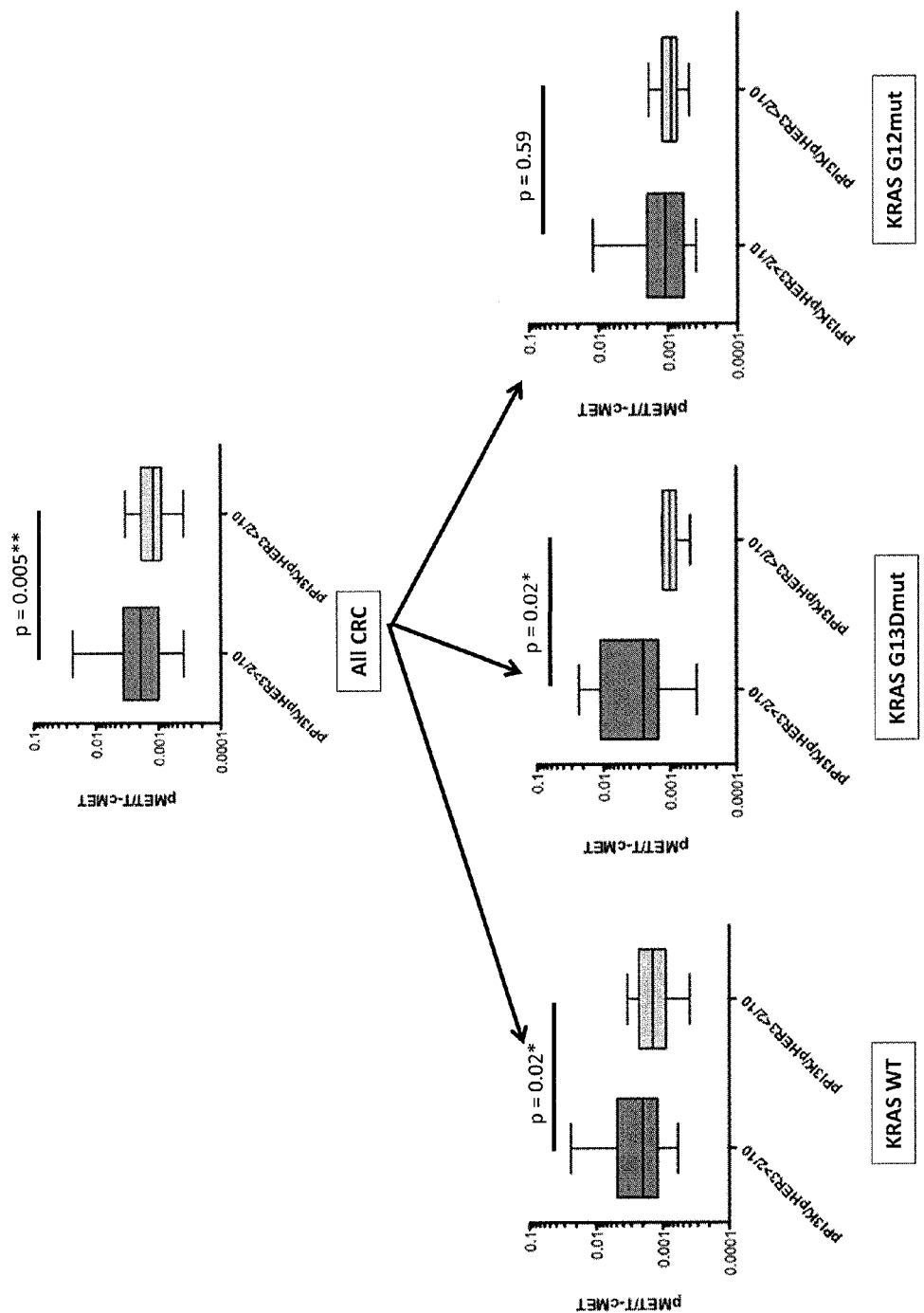
FIG. 13 shows that MET signaling is higher in aggressive (high pPI3K/pHER3 index) KRAS wild-type and KRAS G13D mutant CRCs.
Figure 14:
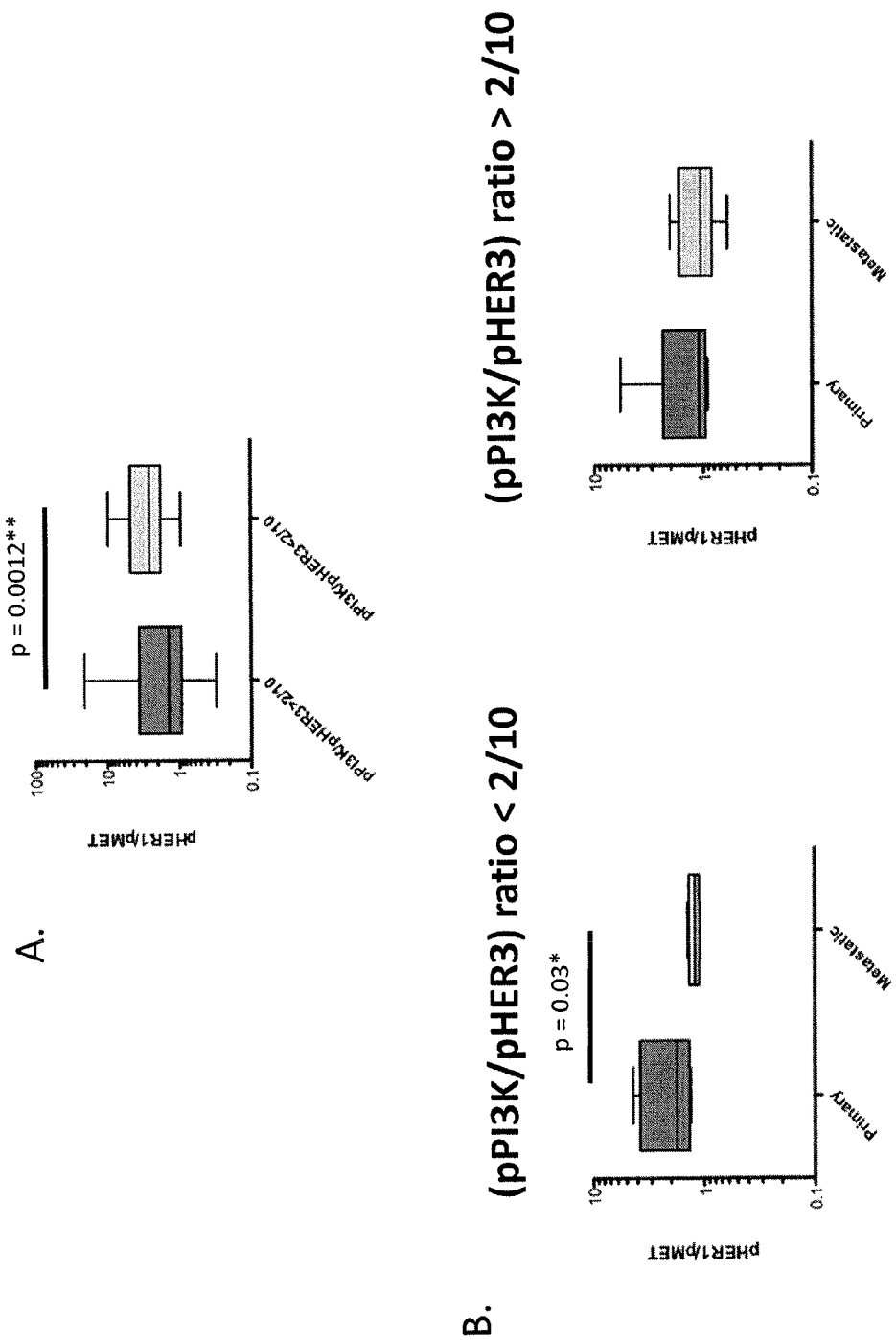
FIG. 14 shows that MET signaling is higher than HER1 signaling in (A) aggressive (high pPI3K/pHER3 index) CRCs and (B) in metastatic CRCs.
Figure 15:
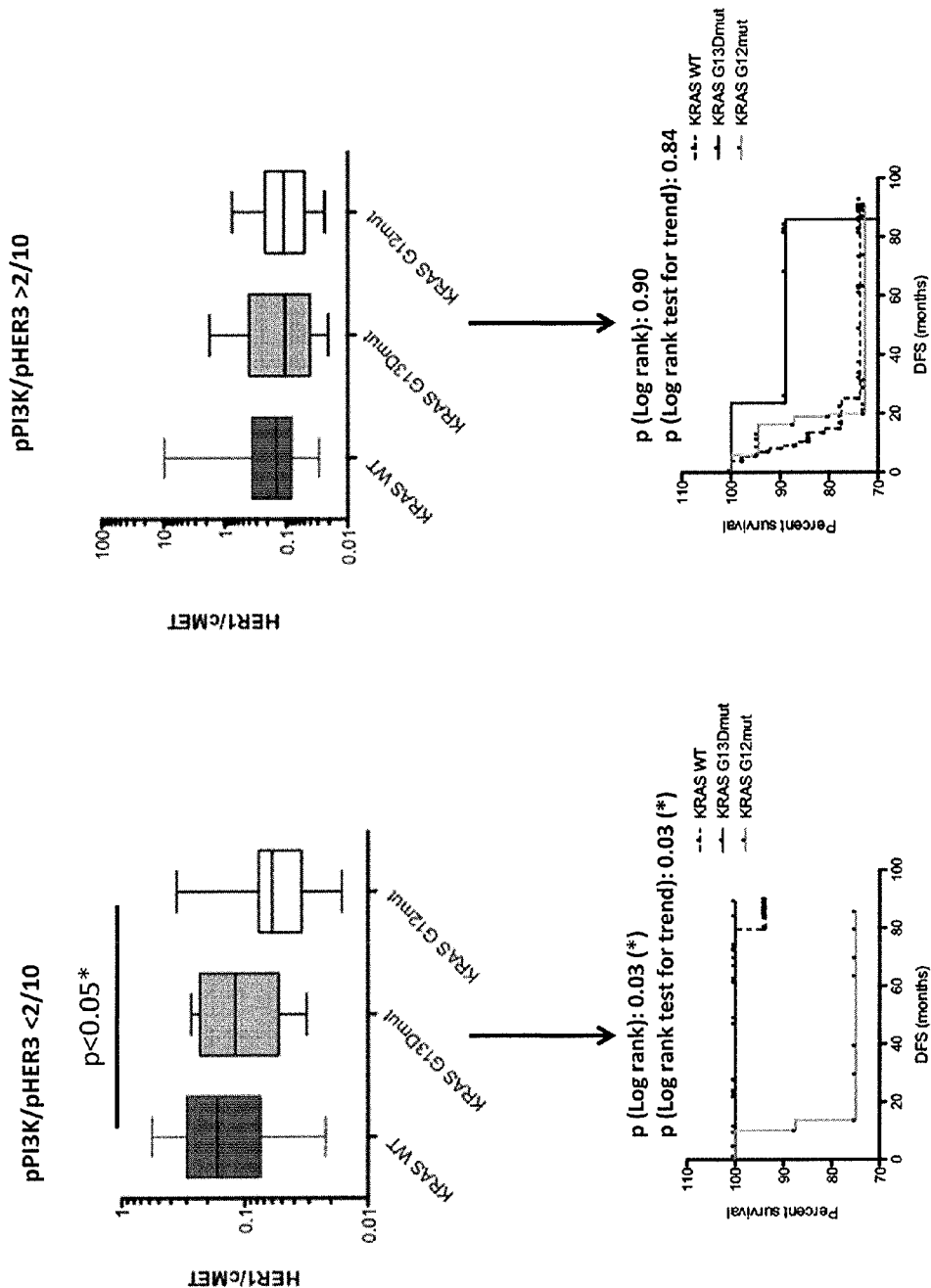
FIG. 15 shows that KRAS-WT CRC tumors demonstrate a significantly higher HER1/cMET index ratio than KRAS G12mut tumors in tumors with a low pPI3K/pHER3 index.
Figure 16:
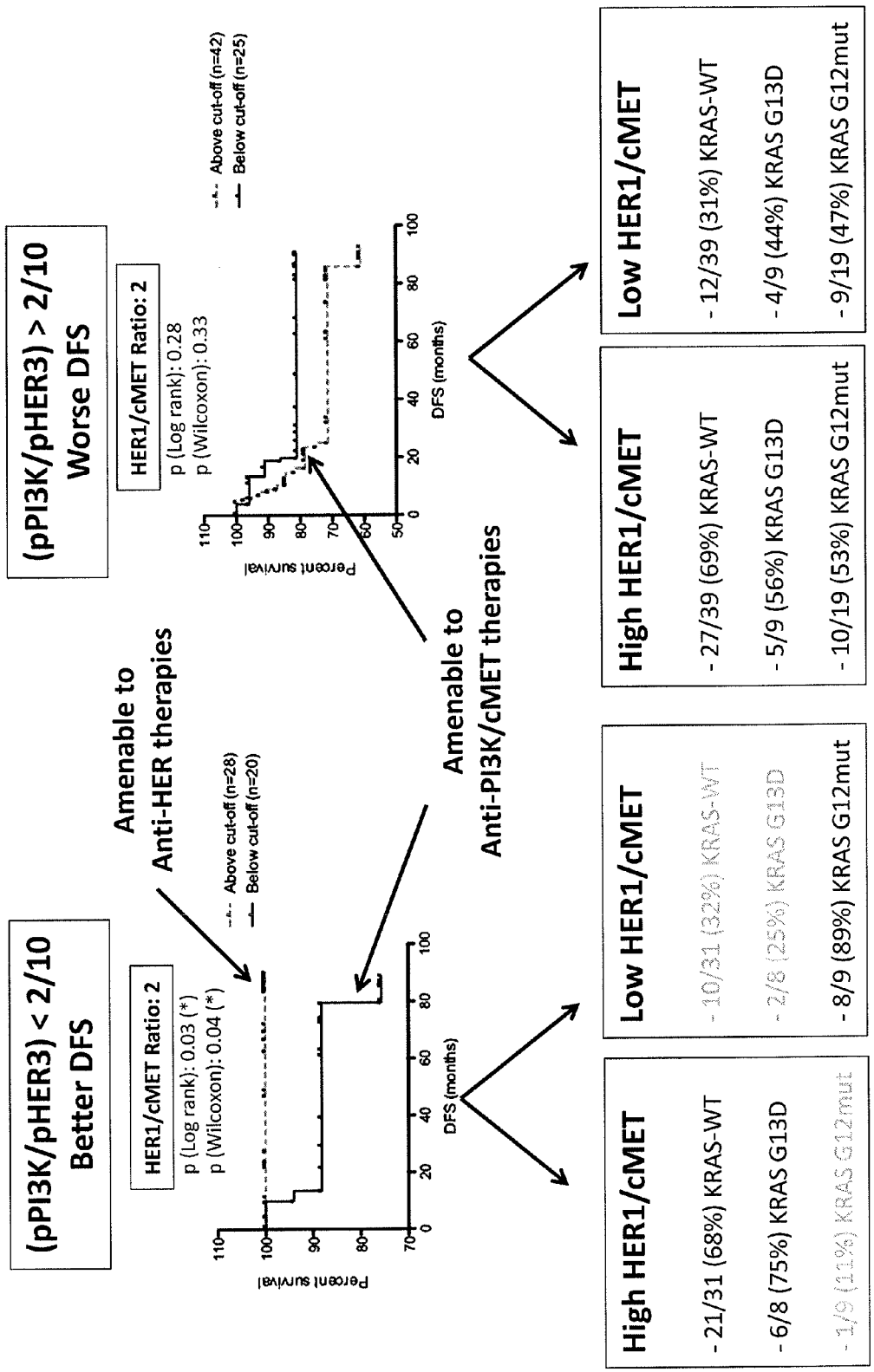
FIG. 16 shows that an appropriate HER1/cMET ratio cut-off selects out the more aggressive KRAS G12mut tumors within the low PI3K population.

FIGS. 13-17 demonstrate that a high HER1/cMET index or low cMET signaling correlates with a low pPI3K/pHER3 index and represents a marker for CRCs with a good prognosis. In particular, FIG. 13 shows that MET signaling is higher in aggressive (high pPI3K/pHER3 index) KRAS wild-type and KRAS G13Dmut CRCs. FIG. 14 shows that MET signaling is higher than HER1 signaling in (A) aggressive (high pPI3K/pHER3 index) CRCs and (B) in metastatic CRCs. The pHER1/pMET ratio decreases as CRCs with low pPI3K signaling metastasize. FIG. 15 shows that KRAS-WT CRC tumors demonstrate a significantly higher HER1/cMET index ratio than KRAS G12mut tumors in tumors with a low pPI3K/pHER3 index. This correlates with a higher DFS in KRAS-WT tumors than in the KRAS G12mut tumors. In contrast, the HER1/cMET ratio is not significantly different among the CRC tumors with a high pPI3K/pHER3 index. This correlates with tumors having a low survival in this cohort. FIG. 16 shows that an appropriate HER1/cMET ratio cut-off selects out the more aggressive KRAS G12mut tumors within the low PI3K population.

Figure 17:
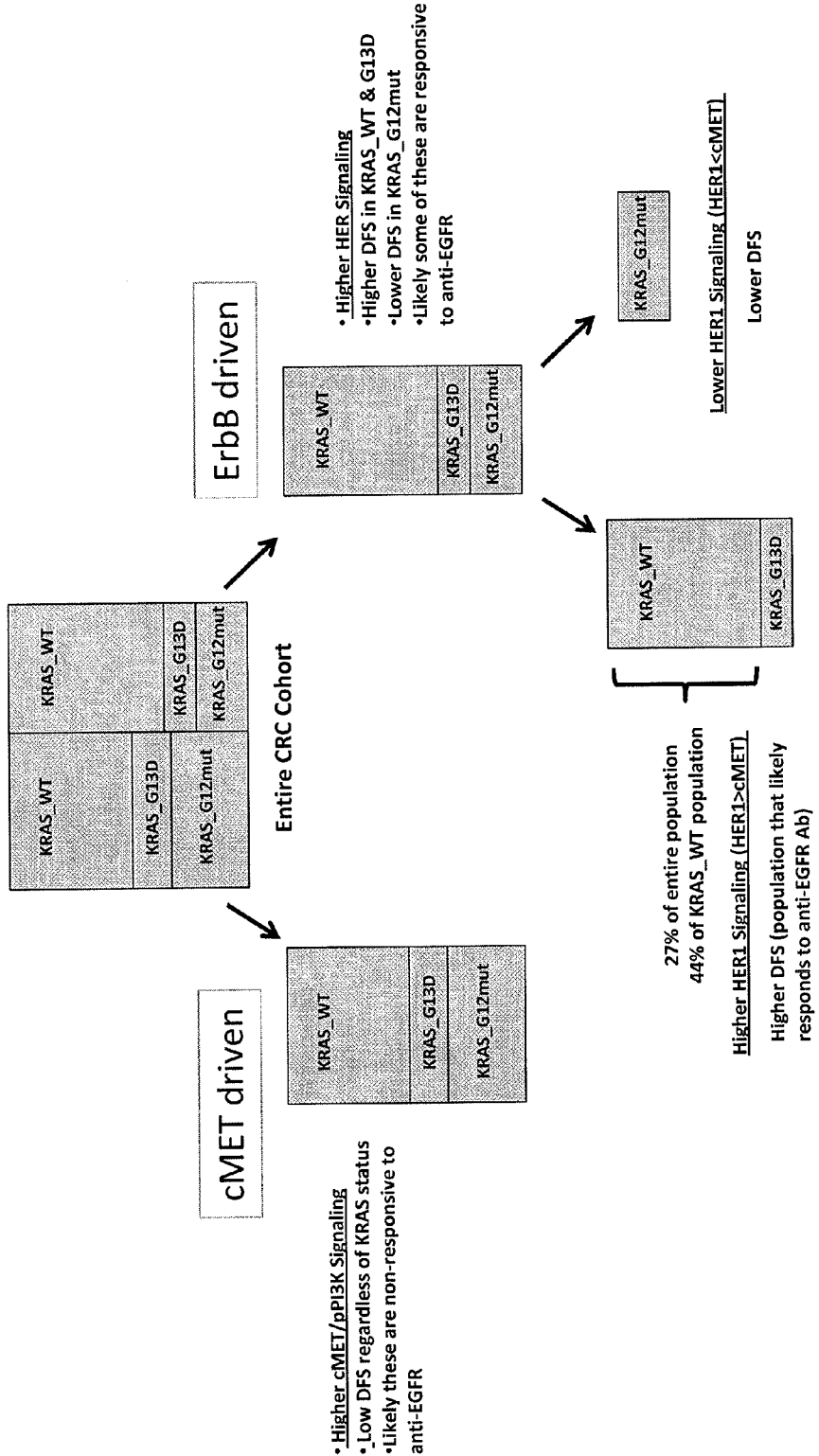
FIG. 17 provides a pictorial summary of a relative/integrated pathway index of the present invention comprising a relative pathway signature+KRAS mutational status.

FIG. 17 provides a pictorial summary of a relative/integrated pathway index of the present invention comprising a relative pathway signature+KRAS mutational status. In HER driven CRC tumors with higher HER signaling than cMET signaling (e.g., HER1>cMET; high HER1/cMET index or low cMET signaling), CRC patients with a WT or G13D KRAS status have a good prognosis (e.g., higher DFS) and are more likely to respond to anti-EGFR therapies. However, in HER driven CRC tumors with lower HER1 signaling (e.g., HER1<cMET; low HER1/cMET index or high cMET signaling), CRC patients with a G12 KRAS mutation have a poor prognosis (e.g., lower DFS).

FIG. 18 shows that pPI3K/pHER1, pPI3K/pHER2, and pPI3K/pHER3 ratios all correlate negatively and significantly with relapse (e.g., the higher the marker, the quicker the relapse) and disease free survival (DFS) in CRC.

Figure 19:
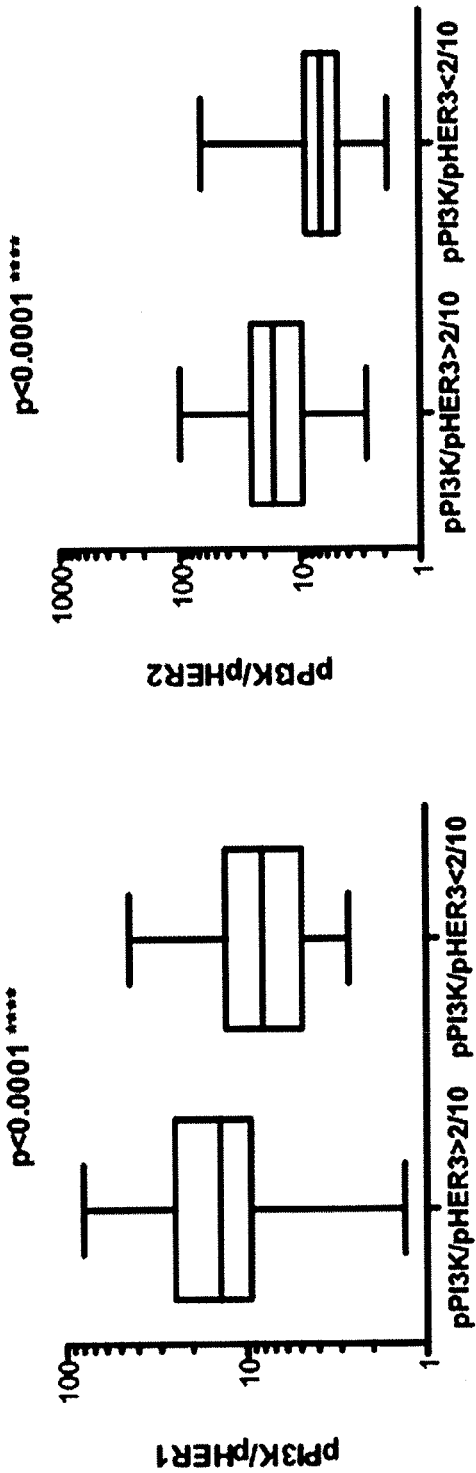
FIG. 19 shows that pPI3K/pHER1 and pPI3K/pHER2 are expressed at higher levels in CRC samples that have higher pPI3K/pHER3 expression (e.g., above the reference pPI3K/pHER3 index cut-off).

FIG. 19 shows that pPI3K/pHER1 and pPI3K/pHER2 are expressed at higher levels in CRC samples that have higher pPI3K/pHER3 expression (e.g., above the reference pPI3K/pHER3 index cut-off).

In sum, this example demonstrates that CEER-based signaling pathway profiles revealed novel molecular subsets of CRCs beyond the KRAS mutation-based segregations. Such molecular segregations can guide novel therapeutic selection strategies for CRCs. In particular, it was discovered that the ratio of pPI3K to pHER3 expression (a pPI3K/pHER3 index) in CRC tumors predicts tumor prognosis and anti-EGFR therapy outcome, regardless of their KRAS status. The best candidates for anti-EGFR therapies were identified as CRCs with a low pPI3K/pHER3 ratio but a high HER1/cMET ratio. A secondary selection of CRC tumors that have low pPI3K signaling (e.g., about 15-30% of pHER3 expression) can further predict CRC tumors with the best prognosis possibly anti-EGFR therapy outcome regardless of their KRAS status. Anti-pPI3K therapies in addition to or instead of anti-EGFR therapies are more suitable for aggressive CRC tumors that have pPI3K signaling greater than about 15-30% of pHER3. Such tumors include, but are not limited to, KRAS-WT tumors with high pPI3K signaling, the majority of KRAS-G12mut tumors, CRC tumors that have metastasized regardless of their KRAS mutational status, etc. This study also found that increased pPI3K signaling may be due to increased cMET signaling in some CRCs. Anti-MET therapies in addition to or instead of anti-EGFR therapies, with or without anti-PI3K therapies, may be useful for the treatment of aggressive CRC tumors that have pPI3K greater than about 15-30% of pHER3. Such tumors include, but are not limited to, KRAS-WT tumors with high pPI3K signaling, majority of KRAS-G12mut tumors, CRC tumors that have metastasized regardless of their KRAS mutational status, etc.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for selecting a therapy for the treatment of colorectal cancer (CRC) in a subject, the method comprising:
   (a) determining a PI3K/HER index which is a ratio of the activation levels of PI3K and a HER receptor in a cellular extract produced from a cancer cell isolated from the subject, wherein the activation levels of PI3K and the HER receptor correspond to phosphorylation levels thereof; and
   (b) administering an anti-EGFR therapy to the subject when the determined PI3K/HER index is less than a reference PI3K/HER index cut-off, wherein the subject has a wild-type KRAS genotype or a G13D mutation in the KRAS oncogene.

2. The method of claim 1, wherein the HER receptor is selected from the group consisting of HER1, HER2, and HER3.

3. The method of claim 1, wherein the reference PI3K/HER index cut-off comprises a value of about 0.2.

4. The method of claim 1, wherein the method comprises determining a PI3K/HER1 index, a PI3K/HER2 index, a PI3K/HER3 index, or combinations thereof.

5. The method of claim 1, wherein the method further comprises determining a HER1/cMET index which is a ratio of the levels of HER1 and cMET in the cellular extract; and administering an anti-EGFR therapy when the determined PI3K/HER index is less than the reference PI3K/HER index cut-off and the determined HER1/cMET index is greater than a reference HER1/cMET index cut-off.

6. The method of claim 1, wherein the subject has metastatic CRC.

7. The method of claim 1, wherein the anti-EGFR therapy is selected from the group consisting of a monoclonal antibody, a tyrosine kinase inhibitor, and a combination thereof.

* * * * *